(12) United States Patent
Harris et al.

(10) Patent No.: US 9,318,030 B2
(45) Date of Patent: *Apr. 19, 2016

(54) PERSONAL TRAINING SYSTEM AND METHOD

(71) Applicant: HAI Logan Gym, LLC, Logan, UT (US)

(72) Inventors: Robert D. Harris, Logan, UT (US); Blake Harris, Logan, UT (US)

(73) Assignee: HAI Logan Gym, LLC, Logan, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/287,444

(22) Filed: May 27, 2014

(65) Prior Publication Data

US 2015/0066170 A1 Mar. 5, 2015

Related U.S. Application Data

(63) Continuation-in-part of application No. 14/012,754, filed on Aug. 28, 2013.

(51) Int. Cl.
| | | |
|---|---|---|
| *A63B 71/06* | (2006.01) | |
| *G09B 19/00* | (2006.01) | |
| *G06F 19/00* | (2011.01) | |
| *E04H 1/12* | (2006.01) | |

(52) U.S. Cl.
CPC ........ *G09B 19/0038* (2013.01); *G06F 19/3481* (2013.01); *E04H 1/125* (2013.01)

(58) Field of Classification Search
CPC ........... A63B 71/0619; A63B 71/0622; G09B 19/038; G06F 19/3481
See application file for complete search history.

(56) References Cited

U.S. PATENT DOCUMENTS

| | | |
|---|---|---|
| 5,435,799 A | 7/1995 | Lundin |
| 5,577,981 A | 11/1996 | Jarvik |
| 7,056,265 B1 * | 6/2006 | Shea ...................... A63B 22/00 482/1 |
| 7,722,503 B1 | 5/2010 | Smith et al. |
| 7,883,445 B2 | 2/2011 | Olrik et al. |
| 7,942,320 B2 | 5/2011 | Joe |
| 7,959,501 B2 * | 6/2011 | Harmon et al. ................... 463/4 |
| 7,959,540 B2 | 6/2011 | Jaquish et al. |
| 7,981,000 B2 | 7/2011 | Watterson et al. |
| 8,128,532 B2 | 3/2012 | Chen et al. |
| 8,157,706 B2 | 4/2012 | Ainsworth et al. |
| 8,172,724 B2 | 5/2012 | Solomon |
| 2004/0162189 A1 | 8/2004 | Hickman |
| 2004/0181129 A1 | 9/2004 | Glasgow |
| 2005/0010426 A1 | 1/2005 | Chen et al. |
| 2005/0209887 A1 * | 9/2005 | Pollner .................. G06Q 50/24 705/3 |
| 2006/0058156 A1 * | 3/2006 | Cohen .................... A63B 24/00 482/4 |

(Continued)

FOREIGN PATENT DOCUMENTS

WO 03079134 A2 9/2003

*Primary Examiner* — Jay Liddle
*Assistant Examiner* — Alex F. R. P. Rada, II
(74) *Attorney, Agent, or Firm* — Kelly & Kelley, LLP

(57) ABSTRACT

A personal training system and method includes generating a personalized exercise regimen for a user, based on user-related data entered into a computerized system. The user moves from booth to booth within an exercise facility to perform different exercises corresponding to the computer-generated exercise regimen for that user. The personalized exercise regimen for the user may be automatically adjusted according to the user's performance results input into the computerized system.

38 Claims, 31 Drawing Sheets

(56) References Cited

U.S. PATENT DOCUMENTS

| | | |
|---|---|---|
| 2006/0189440 A1 | 8/2006 | Gravagne |
| 2006/0223674 A1 | 10/2006 | Korkie |
| 2007/0033068 A1 | 2/2007 | Rao et al. |
| 2010/0042555 A1* | 2/2010 | Ranen .................... A63B 21/00 705/418 |
| 2011/0021954 A1* | 1/2011 | Nakano et al. .................... 601/5 |
| 2011/0281687 A1 | 11/2011 | Gilley et al. |
| 2012/0277891 A1 | 11/2012 | Aragones et al. |
| 2013/0123068 A1 | 5/2013 | Sultan et al. |
| 2013/0253943 A1 | 9/2013 | Lee et al. |
| 2013/0274069 A1 | 10/2013 | Watterson et al. |
| 2014/0081661 A1 | 3/2014 | Fu et al. |
| 2015/0066170 A1 | 3/2015 | Harris et al. |

* cited by examiner

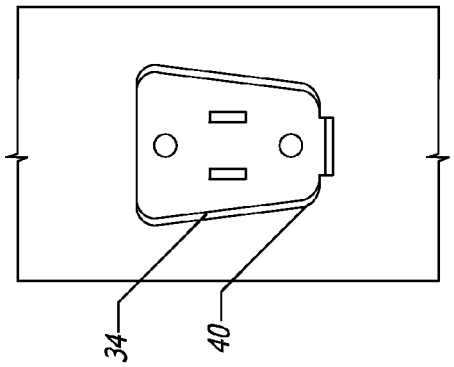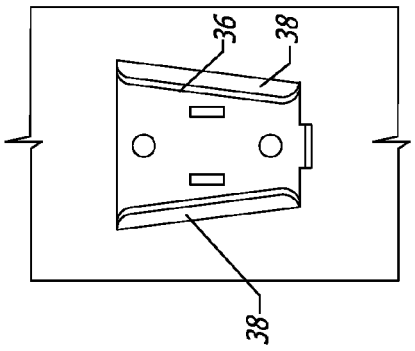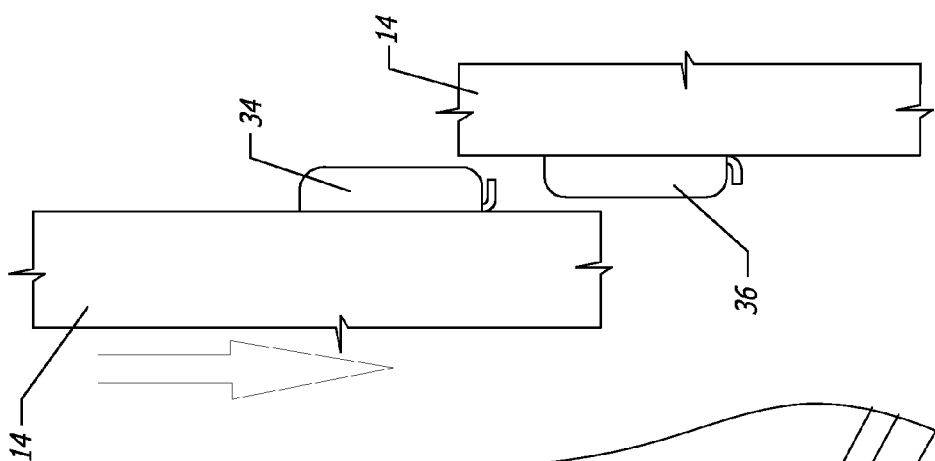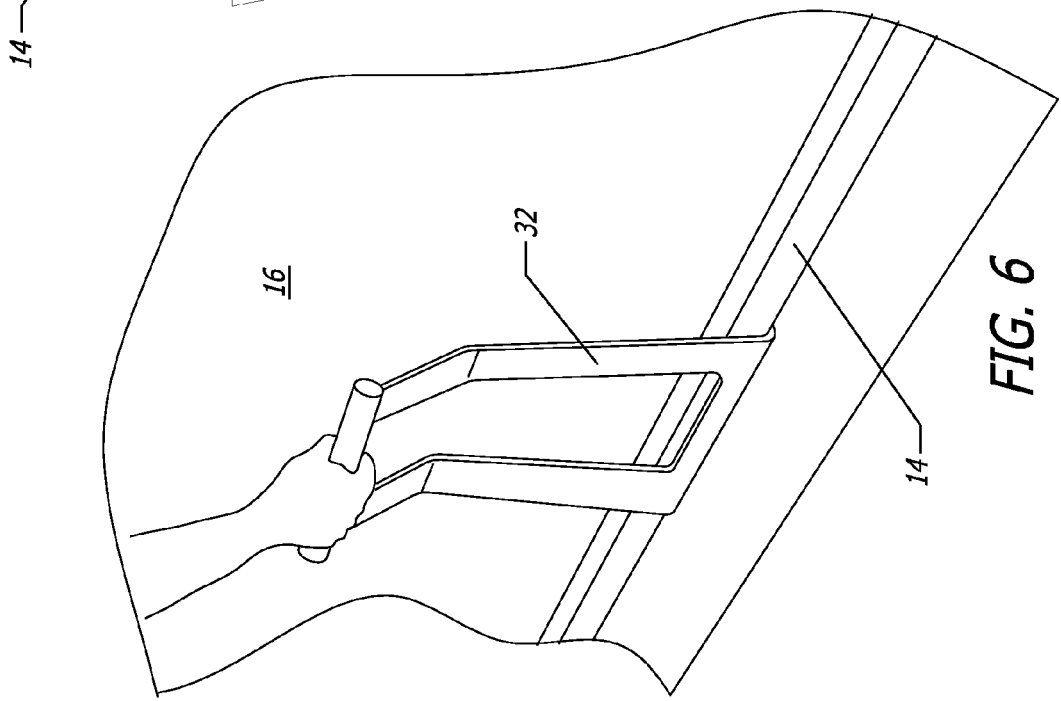

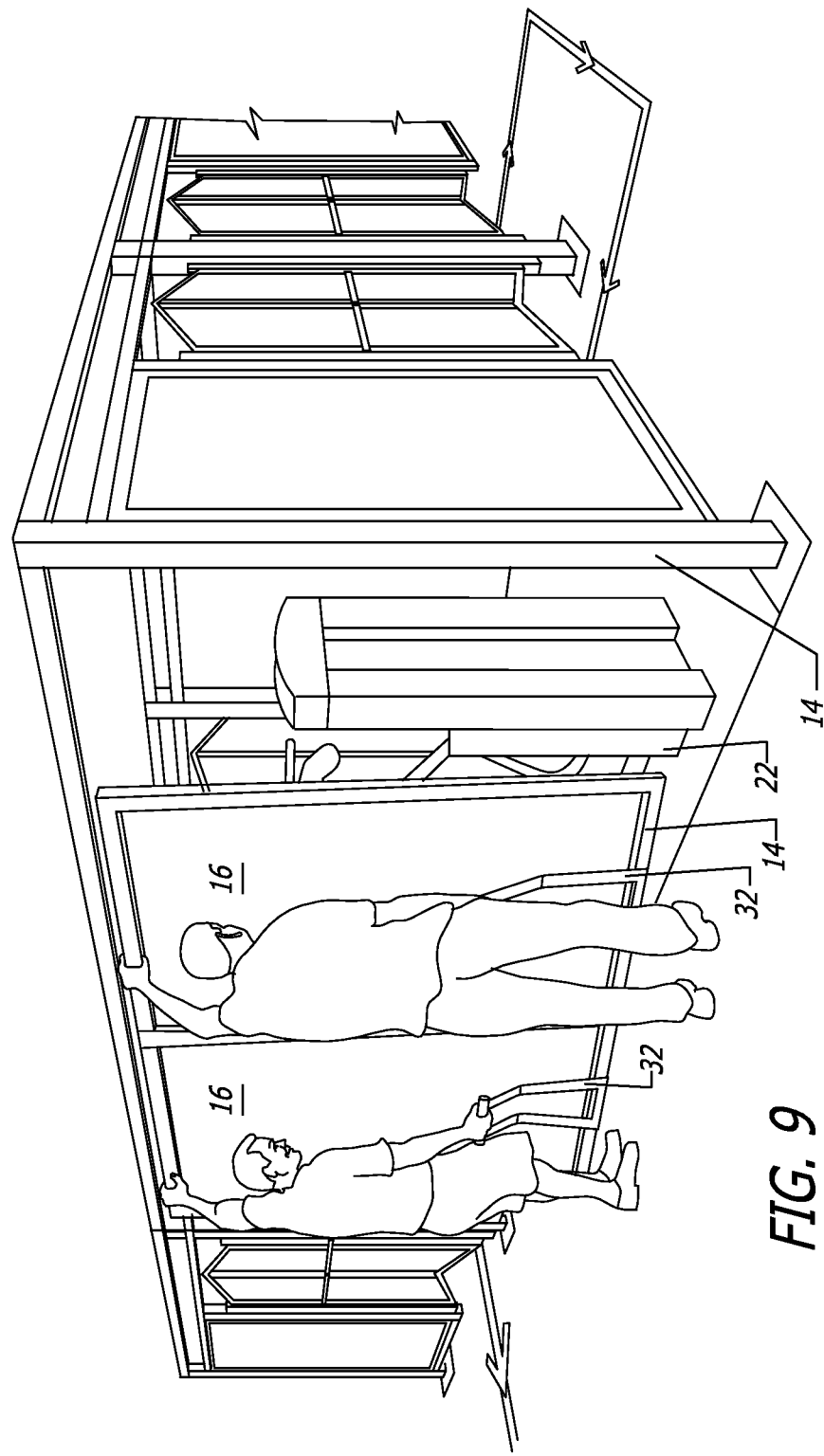

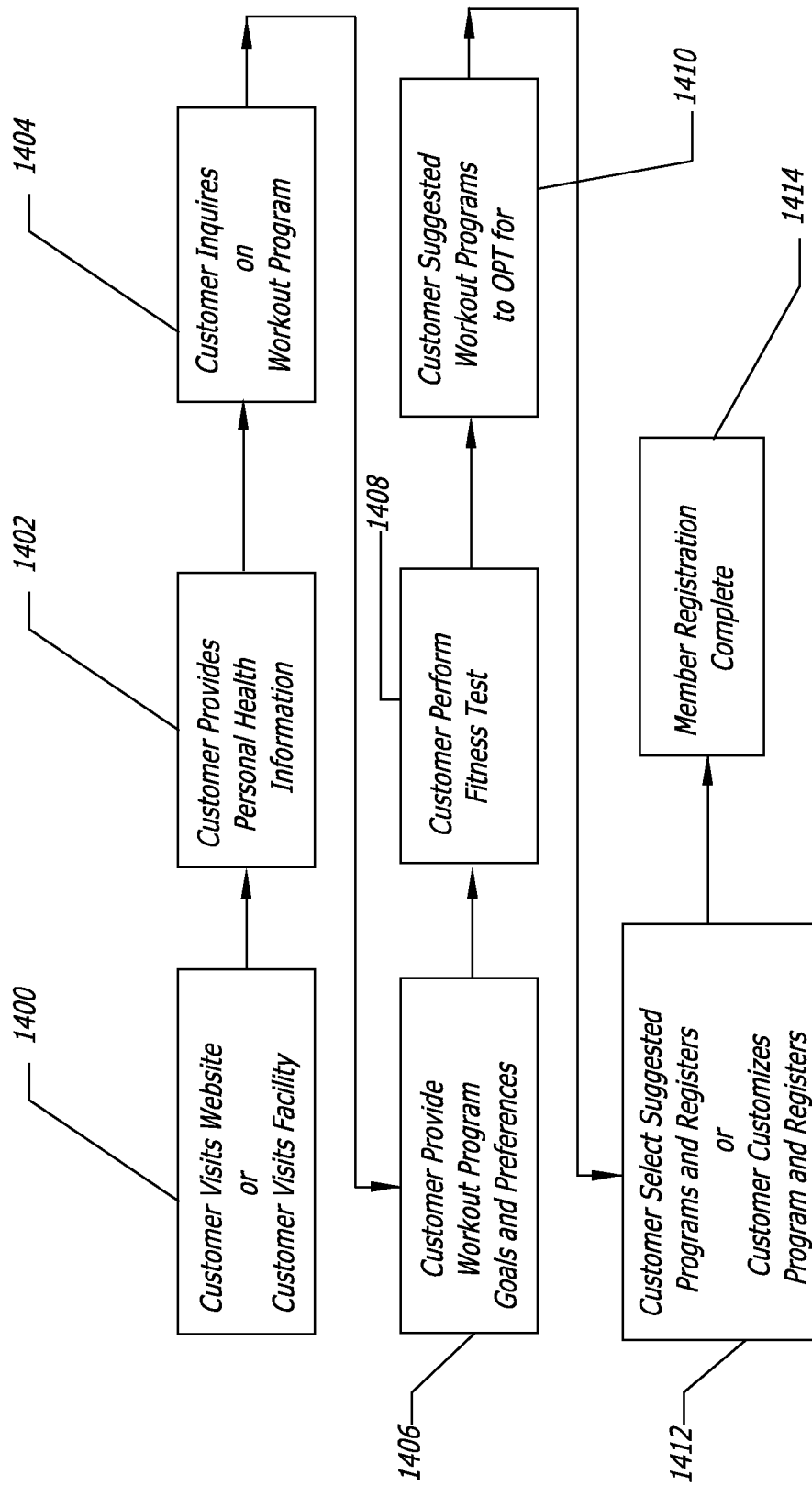

|    | Exercise | Type |
|----|----------|------|
| 1  | Sumo squats | Warmup |
| 2  | Arm Rotations | Warmup |
| 3  | Low back stretch | Warmup |
| 4  | Lunge stretch | Warmup |
| 5  | Rotary stability | Warmup |
| 6  | Rest | Rest |
| 7  | Vib Toe Touch | Vibration |
| 8  | Overhead press | Push |
| 9  | Eagle ab | Pull |
| 10 | Eagle lateral raise | Rotate |
| 11 | Lunge stretch | Full Body |
| 12 | Rest | Rest |
| 13 | Vibration squats | Vibration |
| 14 | Standing calf raise | Push |
| 15 | Ab crunch | Pull |
| 16 | Chest rotation | Rotate |
| 17 | Torso rotation | Full body |
| 18 | Rest | Rest |
| 19 | Vibration sumo squats | Vibration |
| 20 | Eagle calf | Push |
| 21 | Long row | Pull |
| 22 | Tricep press | Rotate |
| 23 | Vertical knee up | Full body |
| 24 | Rest | Rest |
| 25 | Vibration pushups | Vibration |
| 26 | Back ext | Push |
| 27 | Ab crunch | Pull |
| 28 | Glute | Rotate |
| 29 | Squat pull | Full body |
| 30 | Rest | Rest |

FIG. 15

| Member Name | BOOTH #1 Start Time | BOOTH #2 Start Time | BOOTH #3 Start Time | BOOTH #4 Start Time | BOOTH #5 Start Time | BOOTH #6 Start Time |
|---|---|---|---|---|---|---|
| John | 09:00:00 | 09:01:20 | 09:02:40 | 09:04:00 | 09:05:20 | Rest/Review |
| Tom | 09:01:20 | 09:02:40 | 09:04:00 | 09:05:20 | 09:06:40 | Rest/Review |
| Jane | 09:02:40 | 09:04:00 | 09:04:00 | 09:06:40 | 09:08:00 | Rest/Review |

FIG. 19

PERSONAL TRAINING SYSTEM AND METHOD

RELATED APPLICATIONS

This application is a continuation-in-part of U.S. application Ser. No. 14/012,754, filed Aug. 28, 2013, which claims the benefit of U.S. Provisional Application Ser. No. 61/828,489, filed May 29, 2013, U.S. Provisional Application Ser. No. 61/816,510, filed Apr. 26, 2013, and U.S. Provisional Application Ser. No. 61/694,126, filed Aug. 28, 2012.

BACKGROUND OF THE INVENTION

The present invention generally relates to the field of health and fitness. More particularly, the present invention relates to an exercise facility wherein members can exercise privately. Moreover, the present invention relates to a method and system for providing a user with an automated personal exercise program which can be automatically varied according to the user's needs.

Today more than ever before, individuals are becoming more aware of their own physical fitness and the need to exercise. People follow exercise programs for a variety of reasons. These reasons include maintaining general well-being, assisting a weight loss program, increased muscular definition, and preparation for a particular sporting event.

Scientific evidence has established that exercise is known to improve and maximize individual health and to constrain the effects of aging. The proven benefits of fitness training often include, for example, increased muscle mass, lower resting heart rate, decreased cholesterol levels, lower blood pressure, and less stress on joints. To achieve these benefits, a consistent exercise program spanning an extended period of time is usually required.

In order to offer exercisers a complete and balanced program, exercise facilities typically include strength equipment that work targeted muscle groups as well as cardiovascular machines. New exercise facilities or "gyms" are being opened nearly every day to provide a place where individuals can go to work out on various kinds of equipment and physical fitness devices. Modern exercise equipment is typically capable of adjustment to accommodate different fitness levels, i.e., a difficulty or resistance setting is usually provided that can increase or decrease the amount of exertion that it takes to operate the machine, thereby making it possible for a single machine to accommodate users over a wide range of ability levels. Gyms which include such exercise equipment are especially helpful and convenient for individuals who must sit at a desk and work during the day and get very little if any physical exercise, and for a relatively low monthly rate provides access to a fairly large number of exercise devices.

However, traditional gyms provide a limited number of stand-alone pieces of exercise equipment, or stations, on which to accomplish these exercises. Moreover, each device typically can only be used to perform a small set of specifically targeted exercises, for example, a triceps machine is operated by a user to exercise the user's triceps muscles, the target muscle.

The relative popularity of different types of machinery dictates the unique capacity of each machine. For example, men are usually far more likely to use a bench press than they are to use a leg abductor machine. Despite the numerous choices of exercise machines, it is a common occurrence to find increased demand for a certain type of equipment, wherein the demand is often larger than the capacity. Since the devices can only be in active use by one individual at a time, and each individual's exercise program is personal to that individual, there is often contention for pieces of exercise equipment between multiple individuals, resulting in bottle-necking or user downtime. Frequent bottlenecking during peak times is very disruptive to a workout program, often resulting in inefficient and time-consuming workouts. Many times an individual cannot achieve a regular workout and measure the individual's accomplishments because when the individual is ready to exercise with a certain type of equipment, that equipment is being used by another member of the gym. Frequently, if the next station or device is being used by someone else, a person will either cut short a workout session and/or skip one or more stations thereby precluding the achievement of a maximum benefit workout.

Although the multi-fold benefits of physical exercise are well established, most users are pressed for time and seek to maximize the benefit of such time as they have. Due to the increased demands on people's lives, exercisers are requiring more efficient use of their limited time at the gym. At the same time, gym operators typically have limited budgets and are not able to typically purchase more equipment to accommodate increased usage. Additionally, spending money on equipment for purchases requires more floor space into which to fit the additional equipment and increases the total maintenance cost for keeping all the equipment in working order.

Although the above-described problem of not having a particular station or exercise device available when the user desires occurs in some instances, in other instances users are simply overwhelmed with the large number of machines, stations, etc. Given the equipment that is available, the user can create a program from an almost limitless number of possible permutations. This can be overwhelming to those who are starting an exercise program using gym equipment for the first time. The uneducated user may not understand or appreciate the purpose of each of the machines or stations, and may not have a cohesive or effective exercise program. In such instances, the user may utilize only a few machines which they are comfortable with, without realizing the benefits of a fully integrated exercise program.

In the best case, an individual will work with a personal trainer in order to obtain the benefits of experience and customization of a workout for that particular individual. Personal trainers, coaches and the like often desire that the clients under their care and advisement follow a predetermined set of exercises to help the client improve in a desired area or to reach a particular fitness goal or just to prescribe a general fitness protocol or program. However, as might be expected, it can be difficult for a busy client to keep track of the trainer's recommended workout program and to track his or her own performance while following that plan. A strength program must be well planned in order to be effective. For example, a strength program may include exercises for every muscle group at resistance levels based on personal fitness levels. As fitness levels change, the resistance level should also be changed. Planning and tracking is typically a manual process. Workouts are manually recorded in log books by either the client or his or her trainer, in the event that the trainer accompanies and is present with the client during the exercise program.

However, using a personal trainer is expensive. Furthermore, while a personal trainer is useful in some cases, each trainer's knowledge varies and the end experience is random regarding achieving the preferred effects of a customized workout. Aside from monetary considerations by the user, some people are simply not interested in having someone else evaluate their personal performance and look over their shoulder and pressure them to increase their strength and fitness levels. In those instances when a personal trainer is periodically consulted with, the prescribed workout program given to the exerciser by the trainer may not fit the exerciser's ability on any given day. For example, if the exerciser has a cold, didn't get enough sleep the night before, etc., that exerciser may not have the strength or mental fortitude to accomplish the prescribed exercise program.

Of course, providing administrators, trainers, physiologists, and the like increase the gym owner's cost of operating the gym. However, in traditional gyms such individuals are typically necessary to meet the needs of at least some of the member users.

Another disadvantage of traditional gyms is the matter of privacy. The majority of gyms have both male and female users which belong to the gym and exercise there on a regular basis. This can create a level of discomfort in some individuals when working out. There is a wide disparity of muscular strength and fitness levels between these individuals. Some users feel as if they are being judged, looked upon critically, or even "checked out" while exercising. The public nature of gyms creates a fair degree of anxiety and self-consciousness in many members. In fact, many individuals who are interested in obtaining a workout at the facilities provided by a public gym are not willing to attend the gym due to these concerns. There has been a recent development in the opening of women-only gyms where only women are the patrons in order to overcome some of these concerns. However, these women-only gyms also cater to a wide range of women having different muscular strength, fitness levels, body types and the like so that only some of these concerns are alleviated.

Accordingly, there is a need for a new type of exercise facility which addresses the desire for users thereof to work out in privacy, obtain an effective full body workout in a reasonable amount of time, and have access to all necessary equipment during the workout or exercise regimen. The present invention fulfills these needs, and provides other related advantages.

SUMMARY OF THE INVENTION

The present invention is directed to a personal training system and a process for generating and performing a personalized exercise regimen. The present invention addresses the desire for users to work out in privacy, obtain an effective full body workout in a reasonable amount of time, and have access to all the necessary equipment during the workout or exercise regimen.

The system generally comprises a computerized system for generating a personalized exercise regimen for a user. A plurality of booths are provided within an exercise facility, each booth defining an enclosed space configured to be used by a single user at a time and provide privacy to the user within the booth.

The booths are arranged in a sequence in which the user is directed to perform different exercises corresponding to the computer-generated exercise regimen for that user. Each booth is assigned a predetermined exercise to be performed by the user within the booth. The computerized system coordinates the sequence of the user's personalized exercise regimen with the exercises assigned to the plurality of booths. Exercise devices corresponding to the exercises to be performed by the user are disposed within at least a plurality of the booths. Typically, at least a plurality of the booths has a single piece of exercise equipment disposed therein. The user is directed to move from booth to booth according to a predetermined time limit for each booth.

A device may be used for administering a reaction test to the user before exercising. The computerized system receives the user's reaction test results and adjusts the user's personalized exercise regimen according to predetermined reaction test result parameters.

A handheld electronic device, which the user carries from booth to booth during the exercise regimen, is capable of interfacing with the computerized system and receiving and displaying data relating to the computer-generated exercise regimen for the user so as to direct the user to perform exercises within each booth according to the exercise regimen sequence generated by the computerized system for the user.

An electronic screen of the handheld electronic device displays user identification, a tutorial for the exercise, and a resistance or weight to be used during the exercise by the user. Photos, videos, graphic images or animation are displayed on the display screen of the handheld electronic device that instruct the user how to perform the exercise within each booth. The handheld electronic device directs the user to move from one booth to another in a predetermined sequence in order to complete the user's personalized exercise regimen.

The handheld electronic device is capable of inputting user performance results into the computerized system for exercises performed by the user. The handheld electronic device includes a touch screen, a virtual keyboard or physical keys for inputting the user's performance results. The computerized system automatically adjusts the user's exercise regimen according to the user's performance results input into the computerized system.

In accordance with the process of the present invention of generating and performing a personalized exercise regimen, a personalized exercise regimen for a user is automatically generated by entering user-related data into a computerized system. The user-related data includes the step of entering physical attributes of the user into the computerized system, such as age, gender, height, and weight. The user-related data may also include entering results of an initial fitness determination test performed by the user prior to exercising, such as a grip strength test performed by the user. The user-related data entered into the computerized system may also include inputting user-desired fitness program into the computerized system, such as a selection from a general fitness program, weight management program, strength enhancing program, muscle toning program, and a muscle endurance program.

The user may perform a reaction test immediately prior to performing the sequences of exercises. The user's personalized exercise regimen may be automatically adjusted, using the computerized system, based on the reaction test results.

A plurality of booths are provided in accordance with the present invention. Each booth is adapted for use by a single user at a time and each booth is configured to provide privacy to the user in the booth. Each booth is assigned an exercise to be performed in the user's exercise regimen. The user is directed from one booth to another in a predetermined sequence corresponding to the user's personalized exercise regimen and the exercises assigned to each booth.

User exercise performance results for each exercise of the exercise regimen are inputted into the computerized system. The computerized system may automatically adjust the user's personalized exercise program based on the input user exercise performance results.

A handheld electronic device capable of downloading the user's personalized exercise regimen may be provided to the user. Information relating to the exercise to be performed within the booth by the user, according to the user's personalized exercise regimen, may be displayed on an electronic display screen of the handheld electronic device. The user exercise performance results may be entered into the handheld electronic device. The user performance results may be transferred from the handheld electronic device to a server computer of the computerized system.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 6 is a perspective view of a tool used for placing or removing walls of the booths;

FIG. 7 is a side diagrammatic view illustrating interconnection of locking members of booth members;

FIGS. 8a and 8b are male and female interconnecting members, respectively, used in accordance with the present invention;

FIG. 9 is a perspective view illustrating the movement of a wall of a booth, in accordance with the present invention;

FIG. 14 is a flowchart depicting the steps of a member or user registration, in accordance with the present invention;

FIG. 15 is a table depicting an exemplary workout regimen generated in accordance with the present invention;

FIG. 19 is a table illustrating exemplary start times and flow through booths for several users or members of the present invention;

DETAILED DESCRIPTION OF THE PREFERRED EMBODIMENTS

Figure 1:
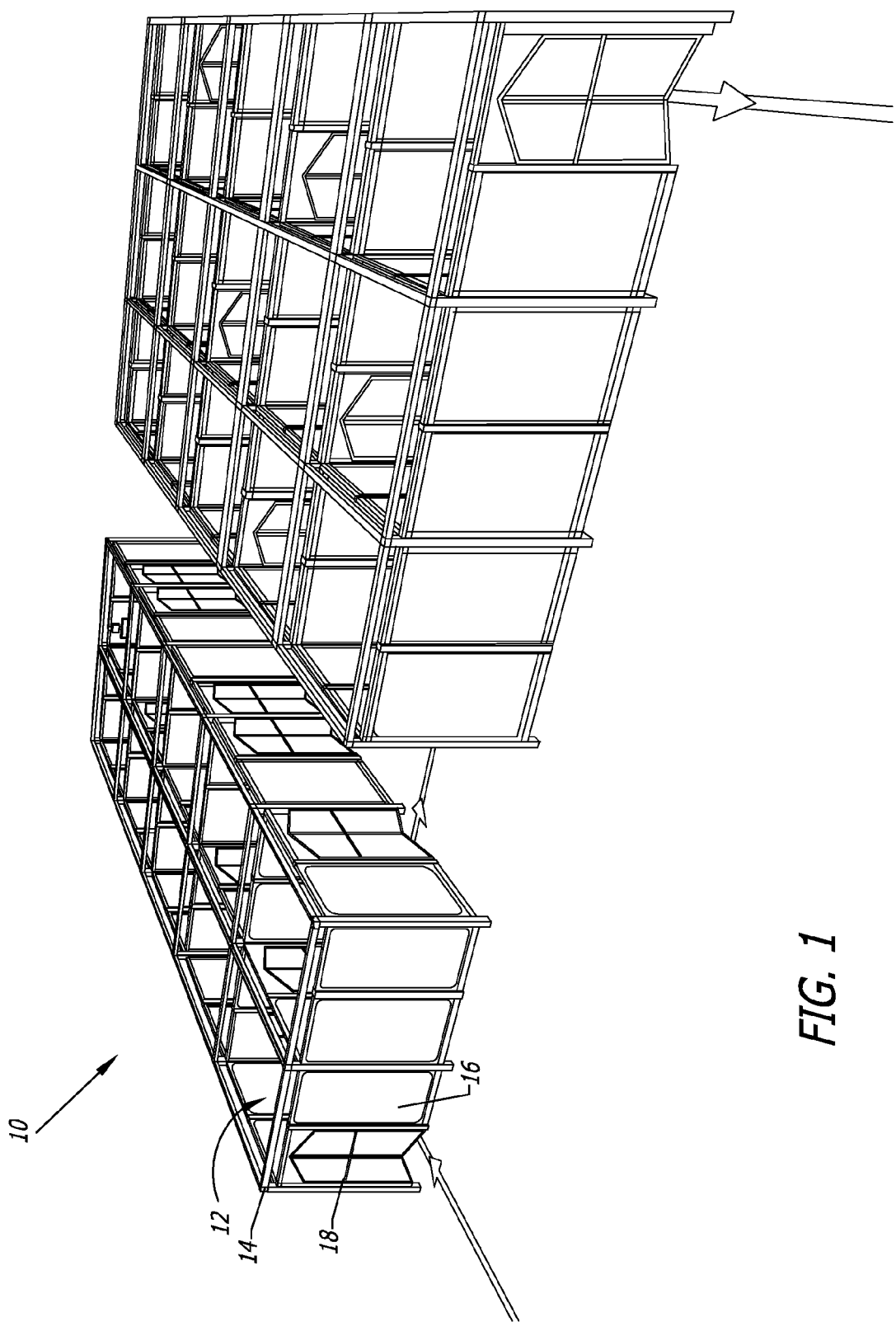
FIG. 1 is a perspective view of a plurality of booths of a workout area of an exercise facility, used in accordance with the present invention.

The present invention is directed to a training system and method that uses a public gym, sometimes referred to herein as exercise facility, wherein each of the users (sometimes referred to herein as members, patrons, clients, individuals or exercisers) is able to perform their exercises in a private setting, so as to overcome the anxiety and self-consciousness of exercising in front of others. Each exercise is performed in a substantially enclosed area, referred to herein as a booth. It will be appreciated that the term "booth" represents a substantially concealed and private area which may comprise an individual room, which may be defined by walls, dividers, curtains, etc. that provides the user anonymity and privacy while performing the exercise.

In a particularly preferred embodiment, an exercise device, such as a piece of exercise equipment or machinery, exercise mats, etc. as needed is placed in each booth, such that the user moves from one booth to another in order to perform a different exercise in each booth using different exercise devices. Typically, the user is provided an individually personalized exercise program, such that the user moves from one booth to another in order to perform different exercises at a level of resistance specific to that user, as described more fully below.

The present invention incorporates a comprehensive, personalized exercise program for individuals that want to be directed by professionals, while maintaining the privacy they desire without having to spend additional funds for a personal trainer. A user who wishes to achieve personal fitness or improve upon sports-related skills is offered a workout program, which is automatically generated by a computer system according to algorithms, data input, and the facilities to achieve their goals within a defined period of time. The workout programs are based on established sports physiology and personal fitness procedures and can be tailor-made to suit the requirements and criteria of each individual. The method and system of the present invention provides users a workout that is unique to the fitness industry in that it is more efficient, user-specific, and cost-effective than traditional training methods.

The method and system of the present invention reduces the need to maintain multiple administrators, trainers and physiotherapists. Instead, the system of the present invention provides an automated solution which can provide a decision-based system that guides the users based on the goals they have set, their profile and medical history, as well as results of a fitness test, reaction test, and results from prior workouts.

The present invention also reduces the manual bookkeeping in terms of both managing the gym facility, memberships, fees, equipment, workout programs, registration and slot booking for training. The present invention utilizes interactive tools such as kiosks, display screens, mobile applications and/or network access to the users to facilitate registration, slot booking and obtaining updates of their achievement from the program.

In order to accomplish these objectives, the present invention provides each patron or user an individualized exercise program, preferably of specifically sequenced exercises, tailor-made to that individual user and adaptable from workout session to workout session. The present invention provides an automated directed workout which guides the user from one exercise to another in a timed fashion, so as to complete a full exercise regimen within an allotted time period. In a particularly preferred embodiment of the present invention, the user performs these exercises in a private setting and receives guidance and is able to provide input via technology incorporated into the system.

With reference now to FIGS. 1-12, the system and method of the present invention includes a gym or exercise facility 10 having workout areas in the form of booths 12 which are adapted for use by a single user at a time and which are configured to provide privacy to the user. Typically, as illustrated in FIG. 1, the exercise facility comprises a plurality of booths 12 such that users, usually members or patrons of the facility 10, can exercise privately and anonymously within each booth 12. The booth, for the purposes herein, means any room, divided area, pod, or the like which provides a sufficient degree of privacy and anonymity and space for the member to perform his or her exercise therein. Typically, a single exercise device or piece of equipment will be disposed within at least a plurality of the booths 12, such that a single member performs an exercise using that device or equipment while in that booth 12. It will also be appreciated that the booth 12 can include an exercise mat or the like, for performing an exercise or stretching which does not require an exercise machine. The exercise to be performed within the booth 12 and/or the exercise device or piece of exercise equipment can be changed over time in order to accommodate the needs of the invention.

Thus, as illustrated in FIG. 1, a single room or workout area of the exercise facility is subdivided into a plurality of different and distinct booths 12. Typically, the booths 12 are present within a single room or area of a gym, although it is contemplated by the invention that the booths 12 may fill a portion of a gym structure, the entire gym structure, be placed on more than one level or floor of the gym, or may be divided and in distinct areas of the gym.

With continuing reference to FIG. 1, each booth 12 may be formed by a framework 14 which supports a plurality of panels 16, which serve as dividing walls. The dividing walls or panels 16 can be comprised of any suitable material, but are typically semi-transparent or opaque so as to provide privacy and anonymity to the member exercising within that booth 12. Moreover, the panels 16 are of a sufficient height so as to provide privacy and anonymity to the member exercising within the booth 12. Such panels or dividers 16 can be of a predetermined height, such as five to seven feet in height, or extend from the floor to the ceiling, as is deemed desirable or necessary. Typically, however, the dividing panels 16 do not extend to the ceiling, but instead are of a sufficient height so as to provide privacy to the user while being able to be sufficiently lit from lighting fixtures placed in the ceiling of the gym, which also provides sufficient air flow throughout the plurality of booths 12.

Figure 2:
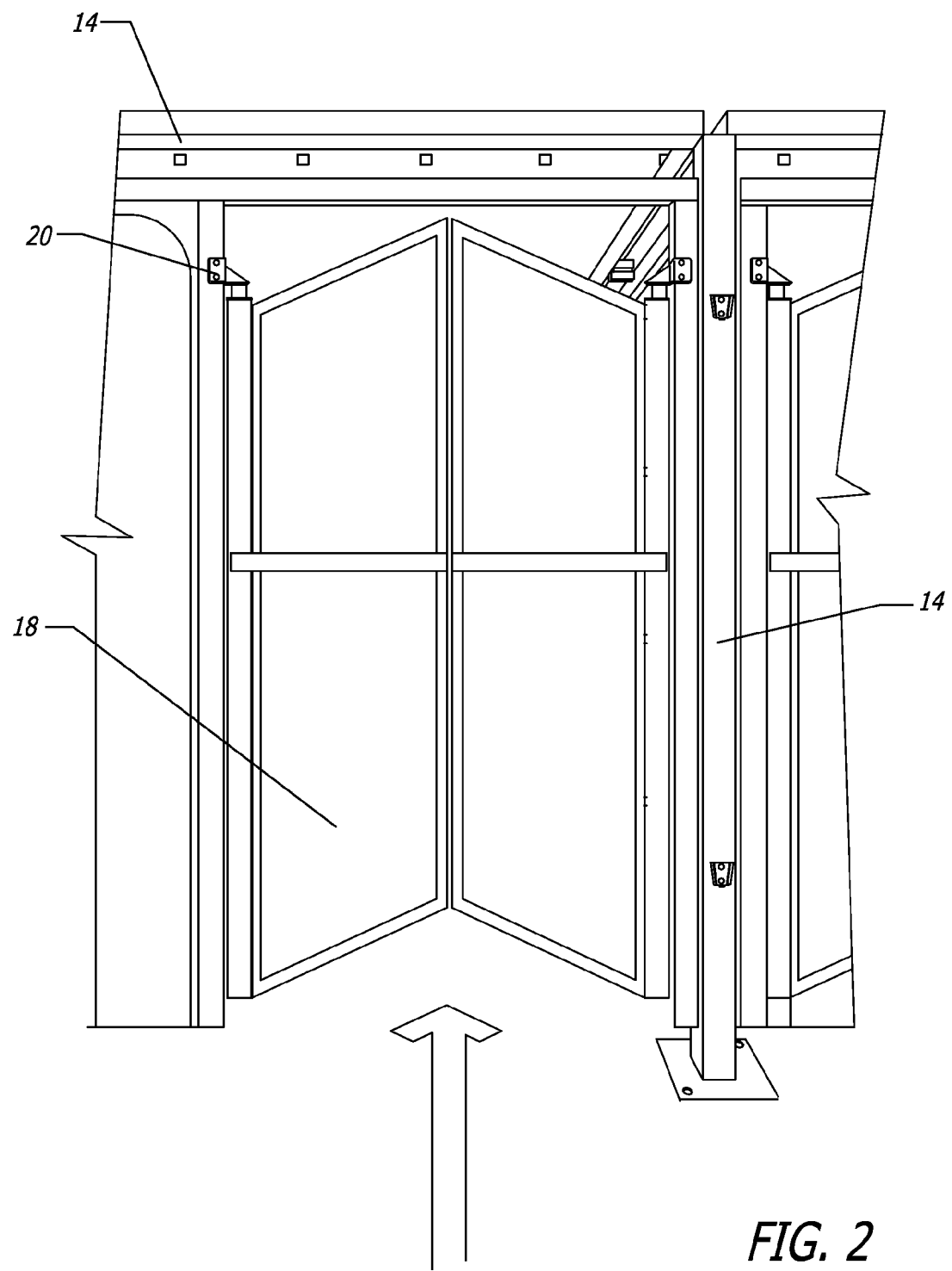
FIG. 2 is a front elevational view of an entrance to a booth.

With reference again to FIG. 1, each booth 12 typically has at least one door 18 for entry and exit. Each booth 12 may have an entry door 18 as well as an exit door 18, which leads to another adjacent booth, as illustrated. FIG. 2 illustrates an exemplary door 18 supported by vertical and horizontal framework members 14. The door 18 may include spring biased members 20 such that the door 18, upon being opened, will automatically close behind the individual entering or exiting from the booth 12. The booths 12 may share dividing walls or panels 16 so as to be immediately adjacent to one another. Entry and exit doors 18 may be shared between at least a plurality of the booths 12, such that a user or member moves from one adjacent booth 12 to another in a predetermined pathway, as will be more fully explained herein. However, it will also be appreciated that the booths 12 may comprise distinct enclosed areas having their own entry and exit, depending upon the configuration and need of the gym or exercise facility.

Figure 3:
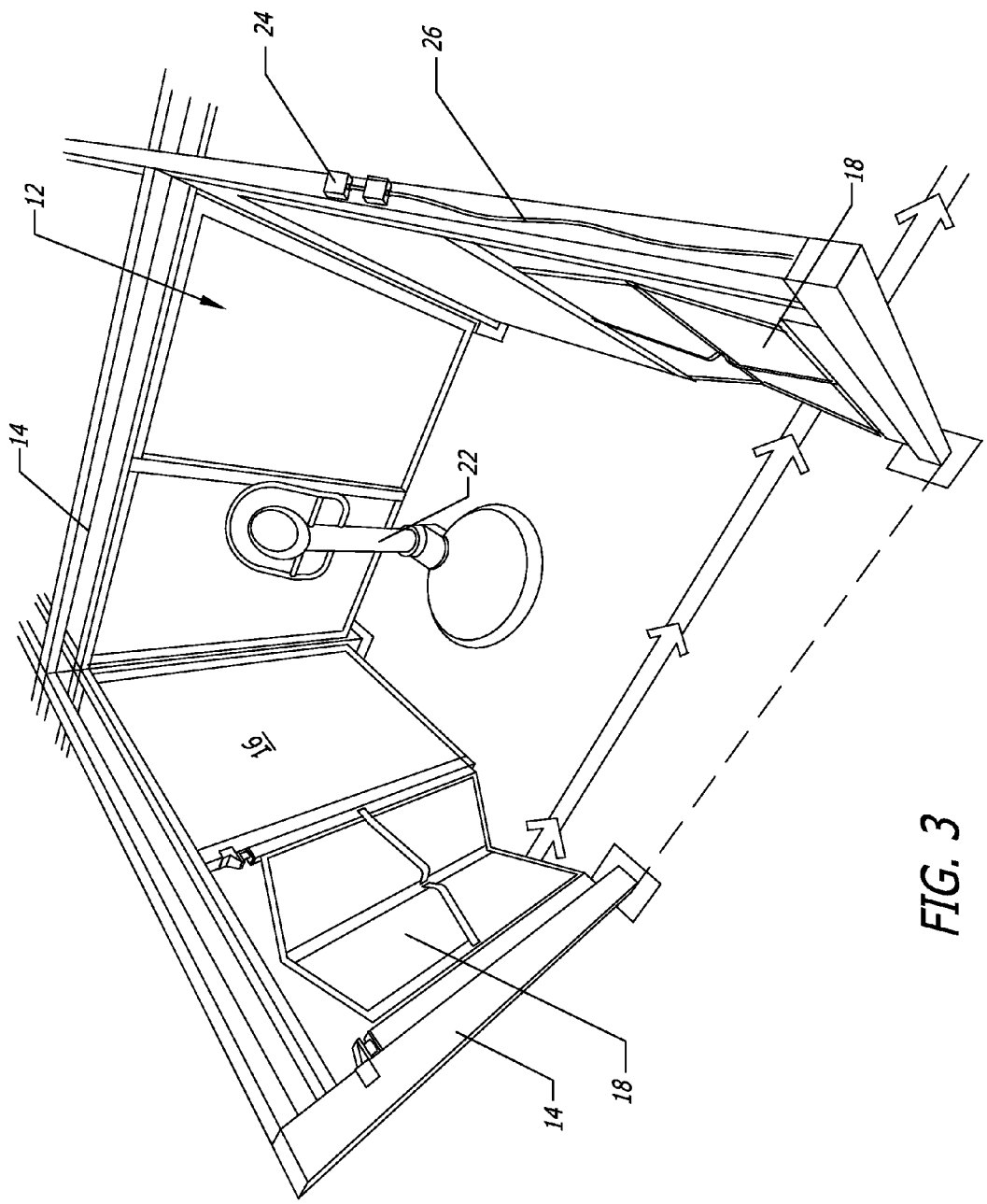
FIG. 3 is a perspective view of a booth, having a wall removed therefrom for purposes of illustration, illustrating an entry, an exit, and an exercise device, in accordance with the present invention.

With reference now to FIG. 3, a booth 12 is illustrated with a side wall thereof removed for viewing purposes. It will be seen that the wall panels 16 substantially encompass the booth 12, typically enclosing four sides of the booth 12 so as to make an enclosed area. Doors 18 provide entry and exit points from the booth 12. The panels 16 and doors 18 are mounted on vertical and horizontal framework members 14. As mentioned above, typically each booth 12 includes a single exercise equipment, device or piece of machinery 22. In this manner, each booth 12 is used by a single member for a single exercise utilizing the exercise device or equipment machinery 22 at any given time. The booths 12 are of a sufficient size so as to accommodate the user, the exercise to be performed, and any exercise equipment 22 therein to perform the exercise. As such, the booth may be quite small, such as fifteen square feet, or large, such as two hundred square feet, but more typically between twenty-five and one hundred square feet in size so as to comfortably accommodate the user and sufficient space for any exercise device and the exercise to be performed while still permitting the gym or exercise facility to provide a sufficient number of booths so as to accommodate a sequence of exercises to be performed by the users in accordance with the invention.

It is believed that the use of individual booths 12 will eliminate distractions which will allow for better concentration and a more effective workout. The privacy and anonymity provided to the member from each booth 12 also eliminates the intimidation or "judge your neighbor" factors which many public gym users dislike, to the extent of being dissuaded from utilizing a public gym. Of course, this will take away much stress and anxiety from these individuals by working out in a private individual booth 12 at each workout station.

Figure 4:
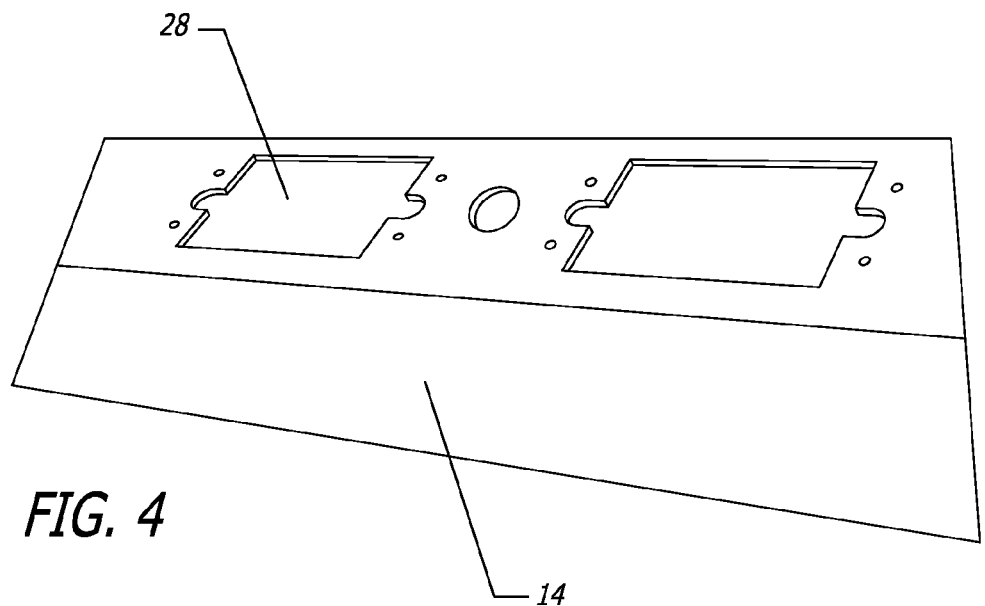
FIG. 4 is a fragmented perspective view of electrical outlet cutouts of a frame of the booth, used in accordance with the present invention.
Figure 5:
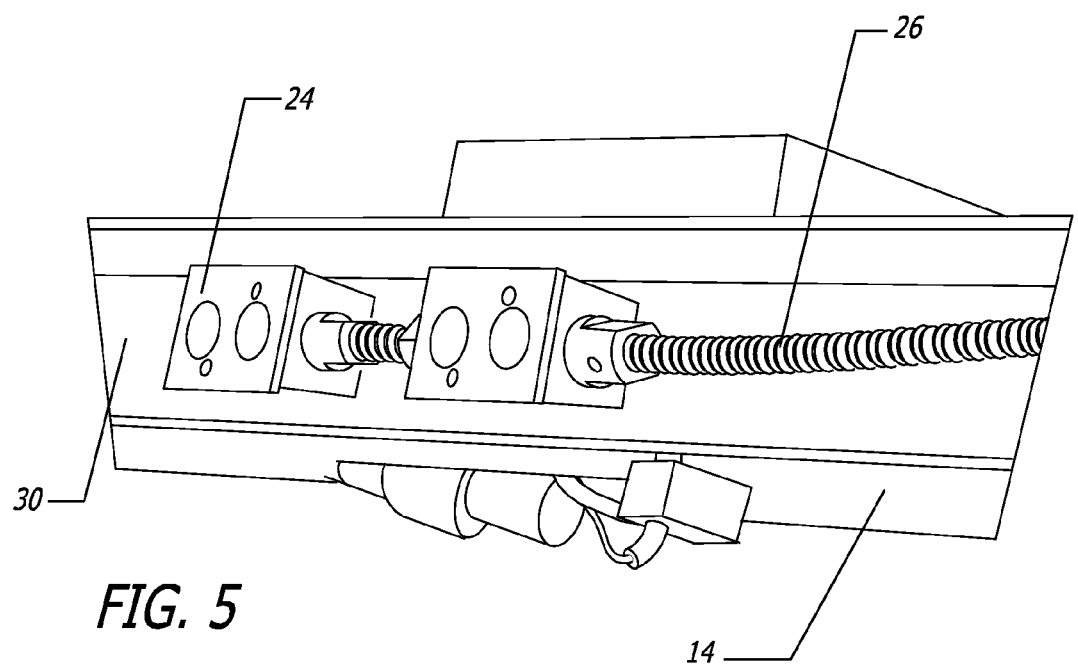
FIG. 5 is a perspective view of electrical wiring and outlets disposed within the frame of the booth, in accordance with the present invention.

As such, the workout area of the exercise facility or gym includes the necessary electrical outlets and plugs 24 and wiring 26 to provide the necessary electricity, cable and/or Internet cabling and access, etc. Preferably, the frame members 14 are able to accommodate such electrical outlets 24 and wiring 26, such as being channeled or the like. For example, as illustrated in FIGS. 4 and 5, framework members 14 may include pre-punched holes 28 for the insertion and coupling of electrical outlets 24, as needed. FIG. 5 illustrates such electrical outlets 24 disposed within or otherwise coupled to such cutout openings 28 and disposed within a channel 30 of the framework 14.

It is also contemplated by the present invention that the environment in each booth 12 can be altered to enhance the exercise experience. For example, the booths may have a certain type or degree of lighting which will be conducive to the user. The air can be conditioned to a desired temperature, humidity, or even desirable smells can be placed into the circulated air of each booth. The color scheme and/or design of each booth can also be altered to enhance the user's experience. It is also contemplated by the present invention that speakers could be used to play music for the individual, and the member user could select from different genres of music or a playlist to be played as a user moves from one booth 12 to another. Of course, the member could also plug in a personal hand-held electronic device to play the member's music within each booth 12 as well.

With reference now to FIGS. 6-10, it may be desirable to periodically replace one piece of exercise equipment with another within a given booth 12. This may be due to the previous exercise device or piece of machinery malfunctioning, becoming aged and obsolete, or to alter the exercise provided within that booth. Due to the enclosed nature of the booths, the entry/exit 18 must be sufficiently large or the panels removable in order to provide access to the internal contents of the booth, such as the removal or insertion of an exercise device 22 therein.

FIG. 6 illustrates a manual lifter tool 32 which can be disposed below a lower edge of the bottom framework 14 so as to lift the panel 16, as illustrated in FIG. 9. This can be done with one or two individuals, as illustrated. The framework 14 of the panels 16, and adjacent framework which is not bolted or otherwise secured to one another, include releasable locking elements 34 and 36, which can serve to lock a panel to an adjacent typically vertical framework 14.

Figure 10:
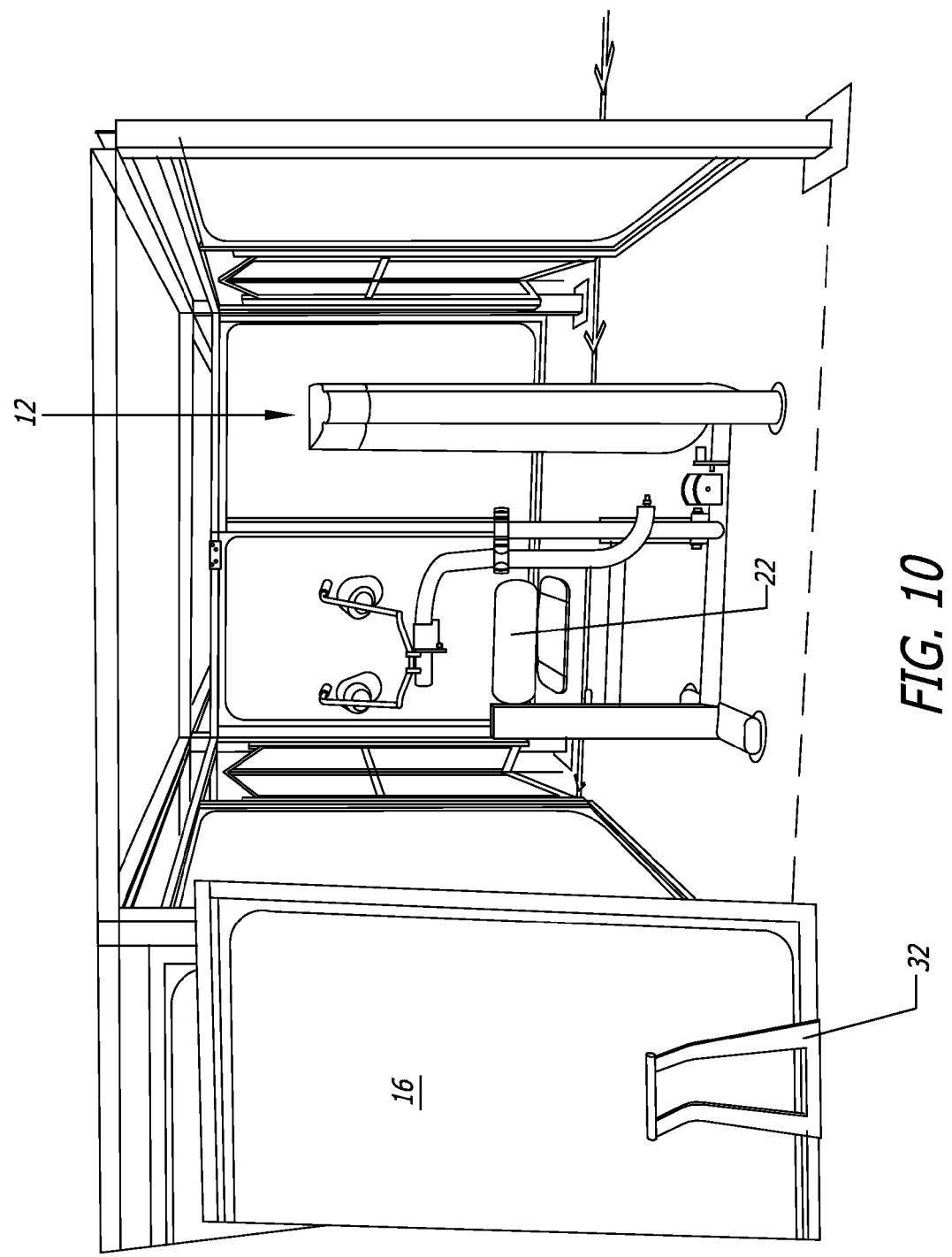
FIG. 10 is a front view of a booth having a wall removed therefrom and used in accordance with the present invention.

FIGS. 8a and 8b illustrate a male locking element 34 and a female locking element 36 which can be slidably engaged with one another so as to lock adjacent panels and/or frame members 14 to one another. As illustrated in FIG. 7, the male locking element 34 is slid into the receiving portion of the female locking element 36. This can be done, for example, by dropping the male locking element 34 into the receiving female locking element 36, which has wings 38 defining gaps or grooves into which the edges 40 of the male locking element 34 slide into. In order to remove the male locking element 34 from the female locking element 36, and thus the framework or panel attached to the male locking element 34 from the panel or framework attached to the female locking element, the panel or framework having one or more male locking element(s) 34 attached thereto is merely lifted with respect to the other framework or panel having the female locking elements 36, as illustrated in FIGS. 6 and 9. This enables the one or more panels 16 to be removed and set to the side while the interior of the booth 12 is accessed, so as to replace, for example, an exercise device 22 therein, as illustrated in FIG. 10.

Figure 11:
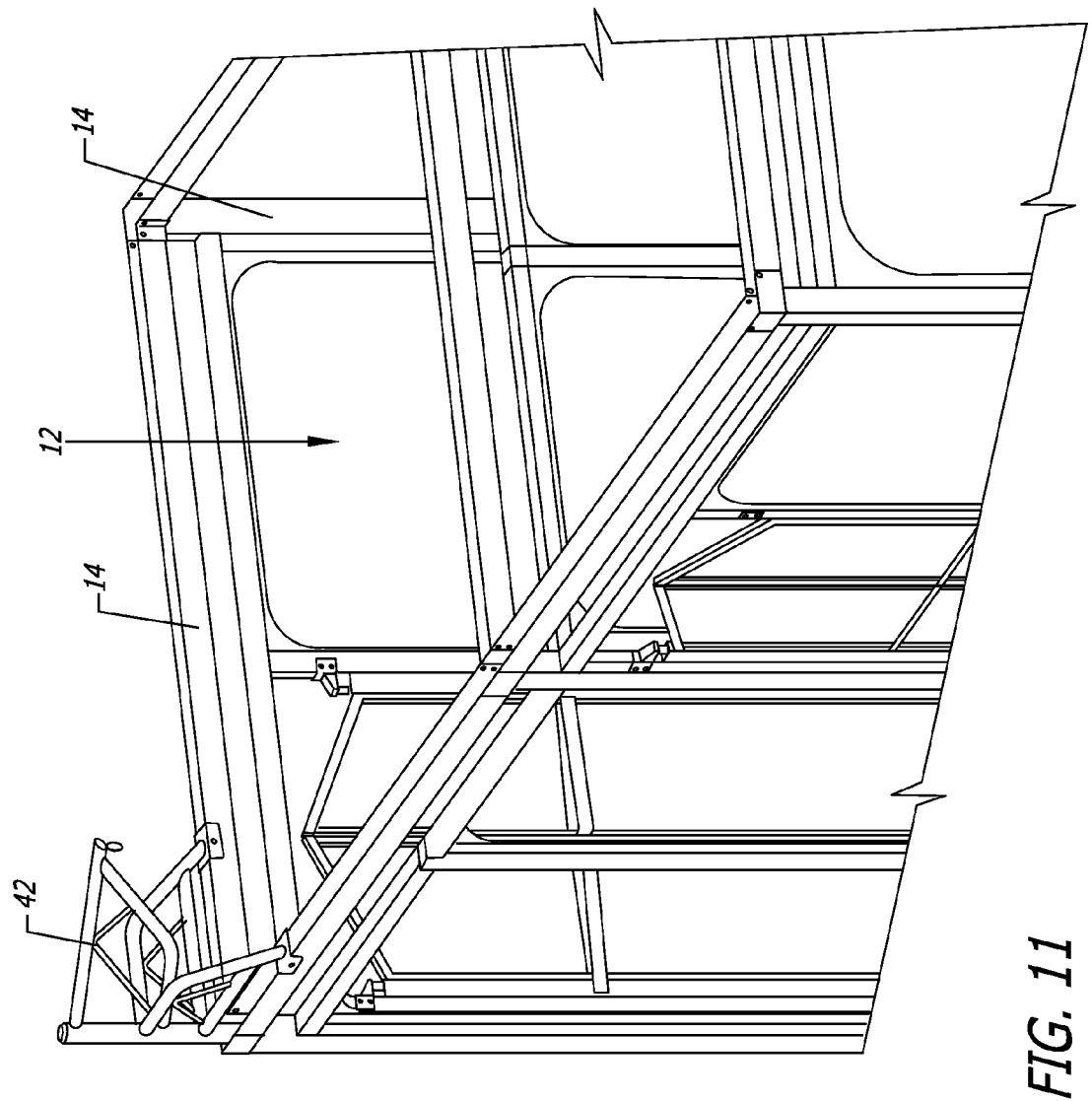
FIG. 11 is a perspective view of an exercise device attached to upper framework of a booth, in accordance with the present invention.

With reference now to FIG. 11, it is contemplated by the present invention that instead of a piece of exercise machinery within the booth 12, an exercise device 42, such as that illustrated in FIG. 11, may be attached to the framework 14 in order to perform the exercise. This can be, for example, a device having a cable and pulley system for performing lat pull downs, triceps pull downs, or the like. Other such devices, such as a pull-up bar, are also contemplated.

It will be appreciated that the size of each booth 12 can be uniform, or adjusted in order to accommodate the space requirements for the exercise to be performed in that booth 12. For example, a booth 12 having a relatively large piece of exercise equipment can be made with varying size panels or multiple panels in order to accommodate the piece of exercise equipment, or a booth 12 in which a lat or triceps pull down device 42, as illustrated in FIG. 11 or having simply a mat for stretches or calisthenics, such as sit-ups will require less space or fewer panels and thus be smaller in size. The interlocking framework 14 of the male and female locking members 34 and 36, and bolts, nuts, or other fastener systems can be used in order to create the desired number of booths 12 and adjust the size of the booths as needed. Typically, the booths 12 are placed adjacent to one another and provide passageway from one to another, as illustrated herein.

In a particularly preferred embodiment, an exercise regimen with a predetermined exercise sequence is provided to the member. This entails the member typically moving from one booth to another booth to perform a particular exercise within that booth, such as performing an exercise utilizing an exercise device 22 within that booth. This further facilitates the member's experience at the gym by means of the member being directed from booth to booth to perform different exercises in accordance with an assigned exercise program such that the member does not need to concern himself or herself with the exercises to be performed that day or to find a piece of available exercise equipment.

In accordance with the present invention, an exercise workout regimen is provided to each member of the gym which is specifically personalized and tailored for that individual, yet consisting of the exercises to be performed in the various booths of the gym. Each workout session may exercise and strengthen all of the major muscle groups of the body of the members. Upon providing information and test results, a personalized workout regimen is provided to each member of the gym which is generated by a computer program of a computerized system.

Figure 12:
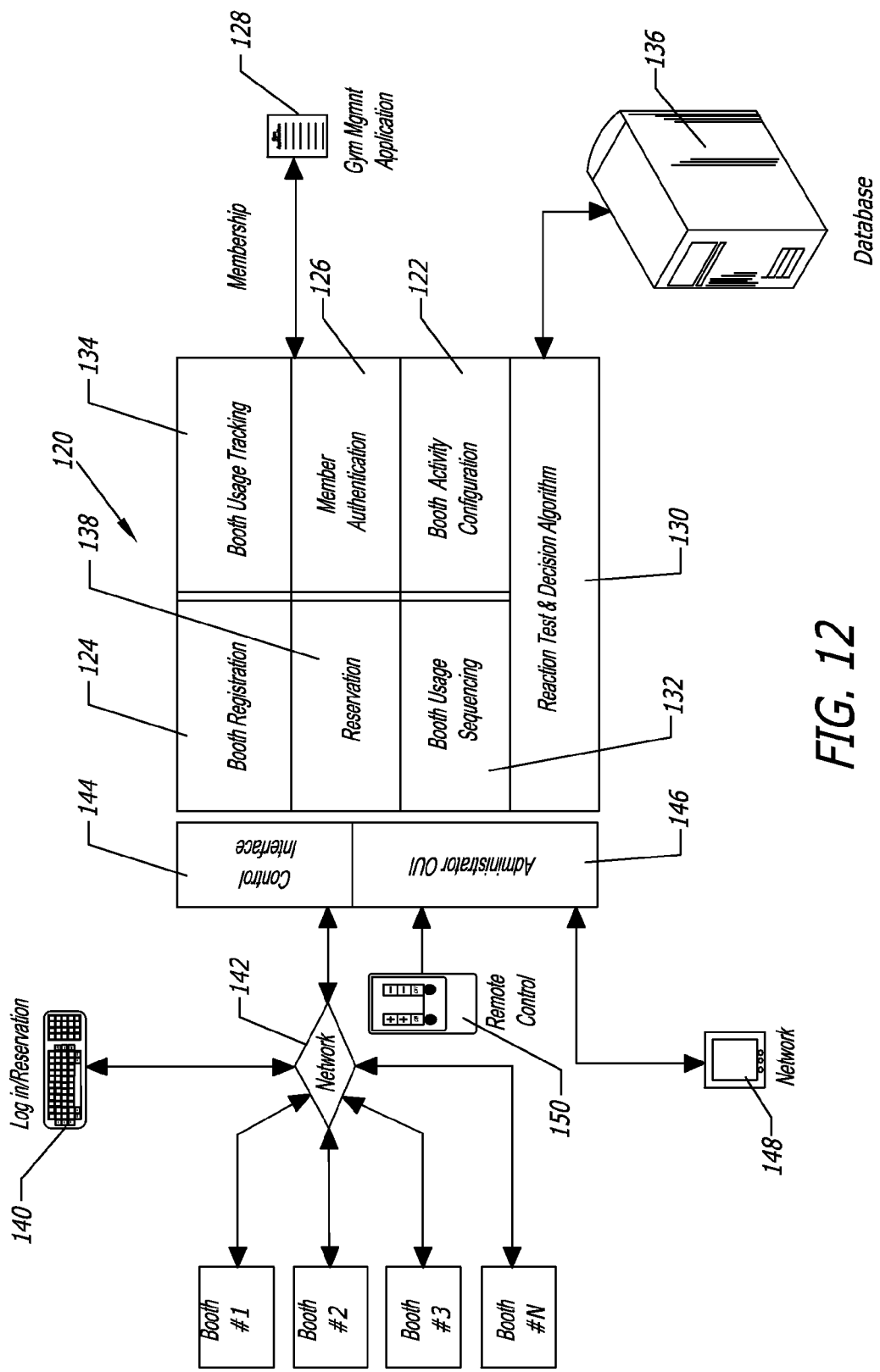
FIG. 12 is a diagrammatic view illustrating an exemplary computerized system used in accordance with the present invention.

With reference now to FIG. 12, an electronic framework of the computerized system utilized in accordance with the present invention is illustrated. This includes the server 120, which may represent a central computer for each gym or location. It is also to be understood that the server 120 could represent additional servers or computers which may be connected to the central computer or server of each gym, in the cloud, or otherwise receive the information from the individual gym locations and/or handheld devices used by the patrons. Clients or users access the server or computers from access channels such as the interactive kiosks placed in common areas, their handheld devices, via the user's computer and an Internet network connection, or via mobile application or the like.

The server 120 may have a variety of configurations, modules, and purposes. The server 120 includes a booth activity configuration module or algorithm 122, which allows the administrator to define the activity for each of the booths and also have relevant information like video or audio tagged to such activities which will be rendered to the user while he is performing the workout.

Booth registration module 124 enables the client to invoke the server and have the activity-related information like the video/audio or other relevant content downloaded locally. Once a particular booth is registered and mapped to a certain exercise activity, the application server may push the data related to the exercise activity onto a local database and computer at the exercise facility, onto a handheld electronic device carried by each user of the gym, etc. so as to avoid the overhead of streaming the video from the server in real time, which could hamper the user's experience.

Authentication module 126 performs member identification, number, card swipe, electronic chip reading, etc. by interfacing with a third-party gym management software 128.

The reaction test module 130 of the server and system provides the capability to prompt the user to go through a reaction test, which shall in turn determine the quantity of reps and/or resistance/weight he or she needs to do for each of the exercises of the user's personalized workout regimen. A decision algorithm stored on the server or other computer shall have the capability to take the inputs from the reaction test and the historical data of the user from his or her previous workouts and generate and define the quantity of reps and/or resistance for each of the exercises. The present invention, in an automated fashion, receives each user's exercise performance results as they are entered into the computerized system, and adjusts the future exercises of the user's personalized exercise regimen taking the past user's exercise performance results into account. Thus, for example, if a user can perform a large number of repetitions of an exercise at a given resistance or weight within the time allotted, the algorithm used by the computerized system of the present invention will adjust upwardly the resistance or weight to be used by the user for that exercise in a subsequent workout.

The system has the ability to define the booth setup procedure or usage sequencing 132, followed by the initialization process where the booth number shall be entered and submitted by the administrator. The server shall validate the request and push the respective data related to the activity that is mapped onto the client's local database. For example, if the administrator inputs the booth number 6, then the relevant exercise activity is mapped to booth 6 on the booth application server and pushed to the client database along with the video and audio and other information related to that booth.

The server tracks 134 the booth activity configuration 122 and booth usage sequencing 132. Each activity or exercise that is offered at the facility such as bench press, push-ups, curls, etc. needs to be defined in the system and should be mapped to the respective booth. The server can accommodate any number of booths, such as booths 1-90, and map each one to an activity where the activity need not be a unique entity. For example, the activity called "bench press" may be mapped to both booth number 1 as well as booth number 18, or later changed from booth number 1 to booth number 7. The booth activity configuration tracks the booth number, the activity type, the benefits of the activity, and the video and/or audio feeds that are tagged to this workout or booth.

With continuing reference to FIG. 12, the server includes or is coupled to a database 136 which contains the member's registration information and periodically updated workout regimens.

A reservation module 138 allows the users to reserve a time to begin exercising at the exercise facility. The login reservation 140 may be done at the gym, or away from the gym, such as at home using the member's computer, or even by means of a smart phone or handheld electronic device. The user logs into a network 142 which interfaces with the computerized system 120 and the various booths (labeled 1-N). An interface 144 is provided between the network 142, the login/reservation means 140 and the booths, etc. An administrator may be provided an interface 146 as well, such as via network 148. This may be done by remote control 150 or at the gym.

Figure 13:
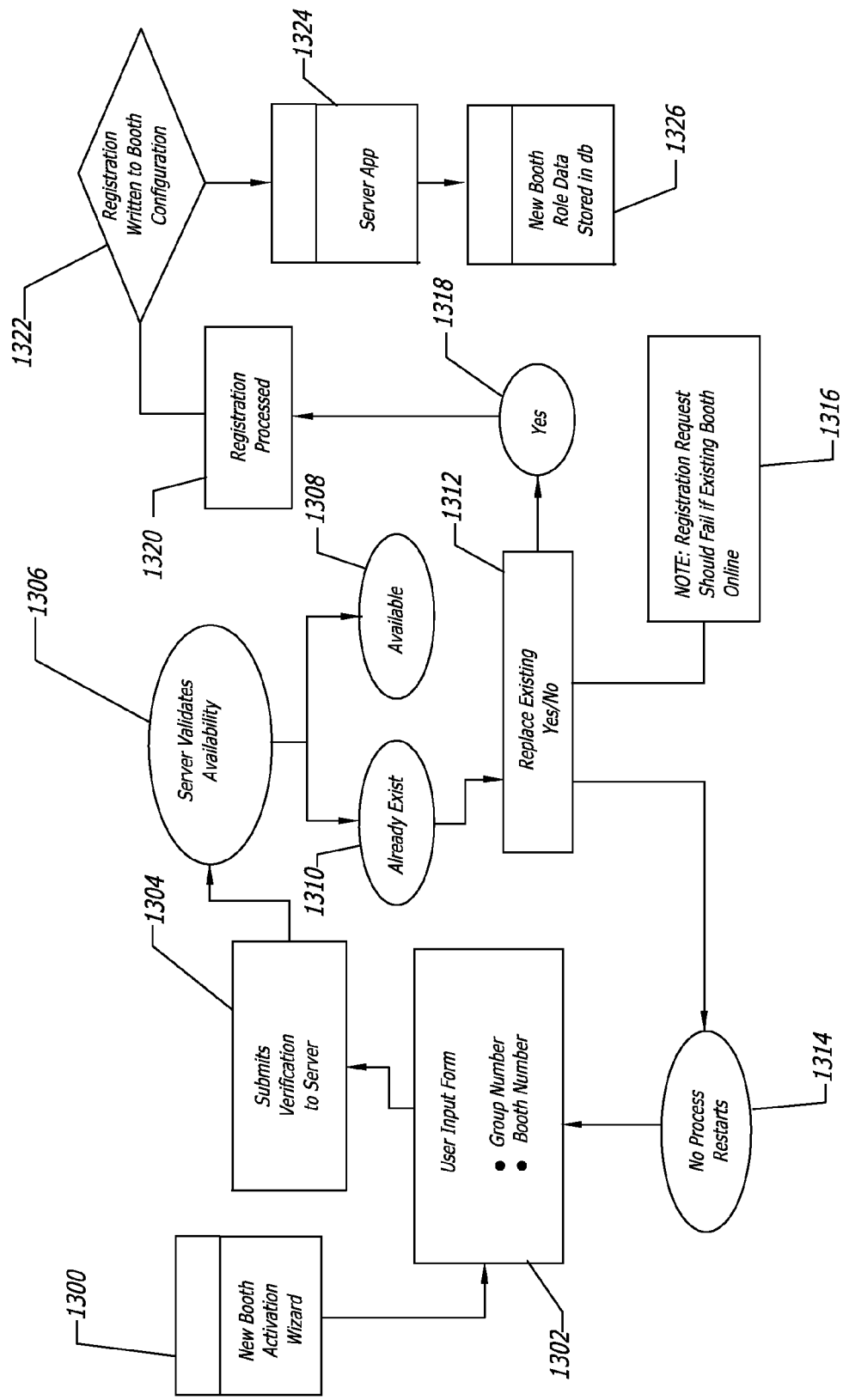
FIG. 13 is a flowchart depicting the steps taken in assigning exercises to a plurality of booths used in accordance with the present invention.

With reference to FIG. 13, software is used in accordance with the present invention to initialize new booths and the booth configuration. This may be done, for example, when a new gym or exercise facility is established, a new sequence of booths are installed, the sequence of the booths are to be changed, or when exercise equipment within the booths is changed or replaced. The new booth activation wizard 1300 receives a user input form providing the group number and the booth number 1302. Verification is sent to the server 1304. The server validates the availability of the booth 1306, and indicates if the new booth is available 1308, or is already in existence 1310. If it is already in existence, an inquiry is provided asking whether to replace the existing booth 1312. If no, the process restarts 1314. If the new booth registration request is being conducted while the booth is online and being used 1316, registration cannot be completed. However, if this is not the case, and if the administrator desires to replace the existing booth 1318, the registration is processed 1320, and the registration is written to the booth configuration and via a server application 1324 is stored in the server database 1326.

Thus, in accordance with the method shown in FIG. 13, a new booth can be added to an existing series of booths, or a booth can be reassigned a piece of exercise equipment or an exercise, and tracked within the server and system in accordance with the method of FIG. 13, such that the computerized system can coordinate the sequence of the user's personalized exercise regimens with the exercises and exercise devices assigned to the booths.

In order for a user to utilize the present invention and have a personalized exercise regimen generated for him or her, a registration process must be completed. With reference now to FIG. 14, the steps undertaken in registering a member are shown. The customer visits the website or visits the gym facility 1400. The customer provides personal health information 1402. Such customer personal and health information may include the age of the user or customer, height, weight, health concerns or ailments, etc. The customer inquires regarding the workout program 1404. The customer provides workout program goals and preferences 1406. For example, the customer or user may desire to be on a weight loss program, a strength training program, a general fitness program, desire to increase muscle mass, increase endurance or toning, or the like.

The customer then performs the fitness test 1408, such as a grip test, which is performed at the gym facility. In order to automatically generate a workout regimen for a member of the gym or exercise facility, the general fitness level of the member is determined. Currently, more experienced and more educated personal fitness trainers have the member max out on every single piece of exercise equipment which the personal trainer plans on using in a workout program for the user. As will be imagined, this takes a significant amount of time and data entry. Personal trainers which are not as skilled or educated, simply set up a workout program of a certain number of repetitions at a certain resistance or weight without any idea of what the individual is capable of, and then adjusts the workout program if the individual either can't perform the number of repetitions at that weight or if the number of repetitions and/or weight is too easy for the individual.

However, in accordance with an embodiment of the invention, the user takes a single fitness test. In a particularly preferred embodiment, this comprises a strength test, such as a grip strength test using a hand dynamometer. This determines the strength of the individual, and it has been found that there is a strong correlation between this test and total body strength. Although the use of a grip strength test is particularly preferred, it will be appreciated by those skilled in the art that other fitness tests or strength tests can be used in its place. The strength test replaces the need to do a maximum test on every single piece of exercise equipment in order to calculate how much weight or resistance should be used in those exercises by the user. The computerized system of the present invention utilizes algorithms associated with the fitness strength test so as to calculate a baseline fitness and strength level of the member without having to do so many tests. Moreover, the results of the strength test set a baseline of weight or resistance for that individual for particular exercises to be performed.

As part of the registration and data entry process, the user may take the fitness test, such as the above-described grip strength test. The user may indicate a desire to attain general fitness, weight management, strength, or muscular endurance or toning, etc. Based upon this desired fitness program selection, the data entered in the health history questionnaire and the strength test results, the computerized system of the present invention generates, in an automated fashion, a workout program for that individual which takes into account all of these factors so as to be personalized and individualized for that particular individual user. This automated analysis is based upon physiological exercise science which is customized for the individual in order to maximize the results the individual is seeking to attain. The computerized system utilizes an algorithm to determine appropriate resistance or weight for the individual to use for the various exercises according to a generated workout regimen.

For example, a young six foot two inch, two hundred twenty pound male having high strength and no health history concerns interested in improving his strength will be given a different workout regimen than another male who weighs three hundred pounds and is interested in weight management, or a five foot three inch, one hundred pound female of advanced age who is interested in general fitness. The computerized system of the present invention can take into account the factors of all three of these individuals and create a unique workout program for each one of them. This can be accomplished even if the equipment or workout stations are the same and the time interval of exercising at each station is the same.

A suggested workout program is provided to the customer to opt into 1410. The customer selects one of the suggested programs and registers, or customizes a program and registers 1412, which completes member registration 1414.

With reference now to FIG. 15, an exemplary exercise regimen of exercises that could be presented to a registered user and incorporated into the present invention is shown. As can be seen from a review of FIG. 15, the exercise regimen includes initial warm-up and stretching exercises, followed by a vibration exercise performed via an exercise device which provides vibration to the user, a push exercise wherein the user will use his or her arms or legs to push, a pull exercise, a rotate exercise, and a full body exercise interspersed with rest periods. The exercise regimen illustrated in FIG. 15 does not include the weight or resistance to be used by the user or a suggested number of repetitions, or a time in which to complete the exercise. The weight or resistance to be used by the user will be provided in the user's personalized exercise regimen generated by the computerized system of the present invention. A target number of repetitions may also be supplied, or the user may merely enter the number of repetitions completed within the time allotted. Typically, the user is provided a set period of time within each booth to complete the exercise, such as between one and two minutes. Thus, the exercise regimen illustrated in FIG. 15 could be completed in between thirty and sixty minutes and provides the user a complete full body workout.

It is to be understood that the exercise regimen illustrated in FIG. 15 is for exemplary purposes only. While providing a full body workout within a predetermined amount of time, the exercise regimen may be changed to suit the needs of the user, the needs of the exercise facility, etc. It will also be understood that if the sequence of a warm-up, vibration push, pull, rotate, full body exercises separated with rest periods are to be followed, as indicated in the right-hand column of FIG. 15, the warm-ups, stretches and exercises corresponding to these in the left-hand column can be changed. It will be seen that some of the exercises may be performed without any exercise device or machine whatsoever, and instead only require a sufficient amount of space and possibly a mat or the like. However, other exercises may require the use of an exercise device or machine, and the machine may be of the type that the user can perform multiple, different exercises as the user rotates through the booths in order to complete the exercise regimen.

In accordance with the present invention, the sequence of exercises in the exercise regimen, such as those illustrated in FIG. 15, would be performed in a plurality of booths 12. The user or gym member would move from booth to booth to perform the different warm-up, exercises, and rest periods. The necessary exercise equipment and devices to perform the exercises within the sequence would be provided within the necessary booths. As described above, the booths are configured and sequenced and the workout regimen provided to the user is similarly configured and sequenced to match that of the sequence of booths. As such, the user moves from booth to booth and performs the necessary warm-up, stretch, exercise, or rest period in order to accomplish the fitness goal of the user in a very scientific and effective manner with minimal thought and input from the user.

Figure 16:
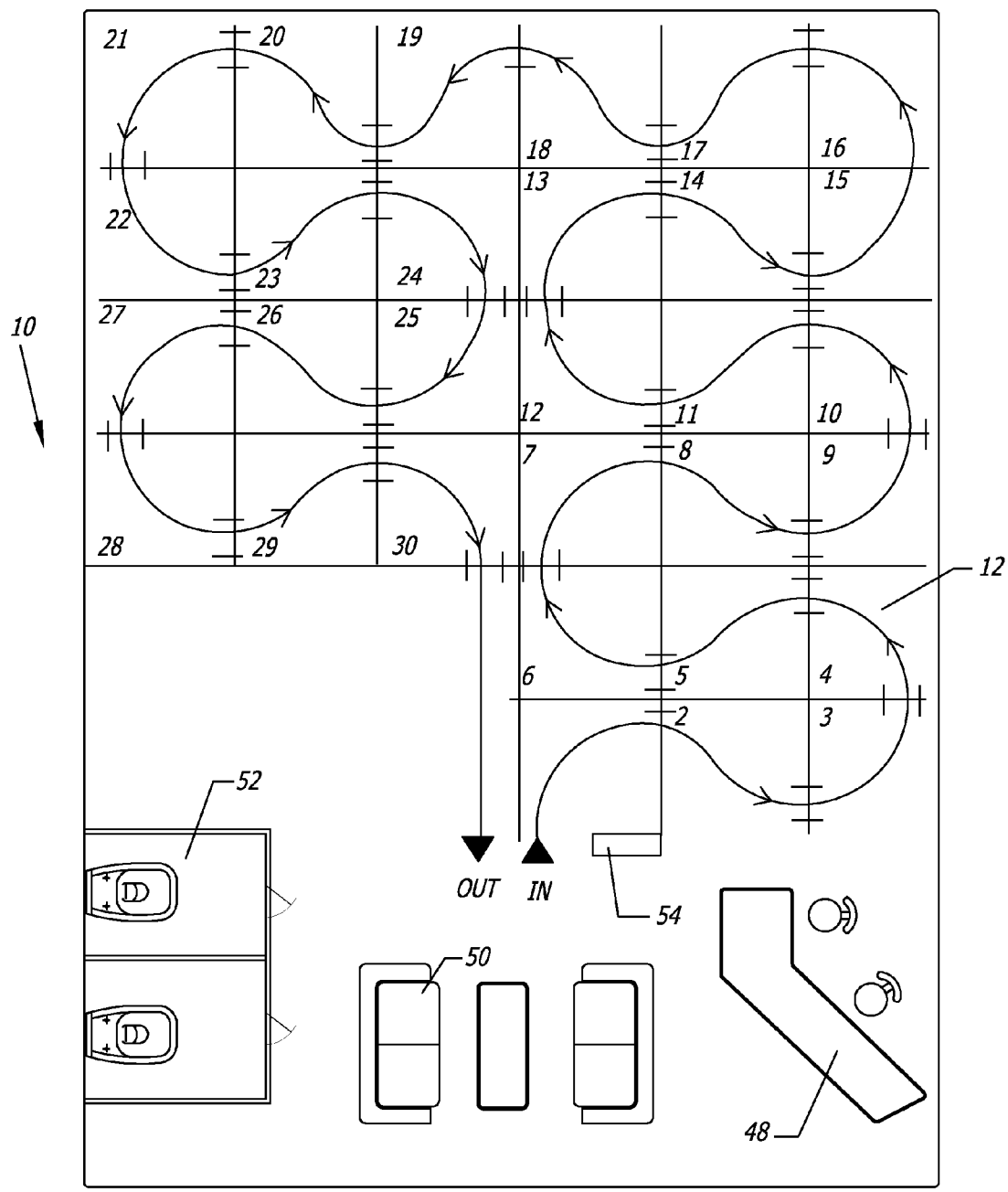
FIG. 16 is a diagrammatic view of an exercise facility embodying the present invention.

With reference now to FIG. 16, the gym 10 has a sufficient number of booths that an entire workout regimen can be performed by moving from one booth to another until the entire workout sequence is achieved.

The gym 10 will typically have a reception desk 48 with employees available to register the member, assist the member in beginning the workout, etc. A waiting room 50 and restrooms 52 will typically be provided. A kiosk or display monitor or the like 54 may be provided, such as outside the initial booth, for the member to log in and perform a reaction test. The member then proceeds through the various booths 12 (numbered 1-30 in FIG. 16), performing a different exercise or a rest period. In the case of providing one minute of time to perform the exercises or rest within each booth 12, in the arrangement illustrated in FIG. 16, the member's workout would last thirty minutes.

Although only one member would be in a given booth 12 at any given time, it will be appreciated that multiple members could be exercising within the booths and the gym at the same time, but be present in different booths so as to follow the sequence of other members. In the arrangement illustrated in FIG. 16, with a total of thirty booths, up to thirty gym members could be present and performing their exercises according to their individualized workout regimens at any given time. Of course, when the first member left the last booth, another member could enter into the first booth to begin his or her workout regimen, such as every minute. The computerized system of the present invention allows members to schedule a specific time to begin their workout, and then moves that member from the first booth through each of the series of booths until the workout session is completed. It will be appreciated that each booth at any given moment may have a different member of the gym therein performing an exercise. All of the exercises are specifically timed, such that each gym member in a given sequence or series of booths finishes his or her exercise for that specific booth at the same time, and is provided an allotted amount of time to enter in the results of their exercise, typically in the form of the number of repetitions performed. All of the gym members are then given an allotted time to move to the next booth, such that gym members are moving from one booth to another at approximately the same time, such that there is only a single member within a booth at a given time.

It will be appreciated that each booth 12 includes a workout station, which can comprise a mat for performing stretches or manual exercises, such as sit-ups, push-ups, etc. Alternatively, an exercise device or piece of machinery is disposed within each booth for performing a particular exercise. Typically, only a single piece of exercise equipment or machine is in each booth, such that the user performs only a single exercise, according to the resistance/weight provided by the personalized exercise regimen.

Figure 17:
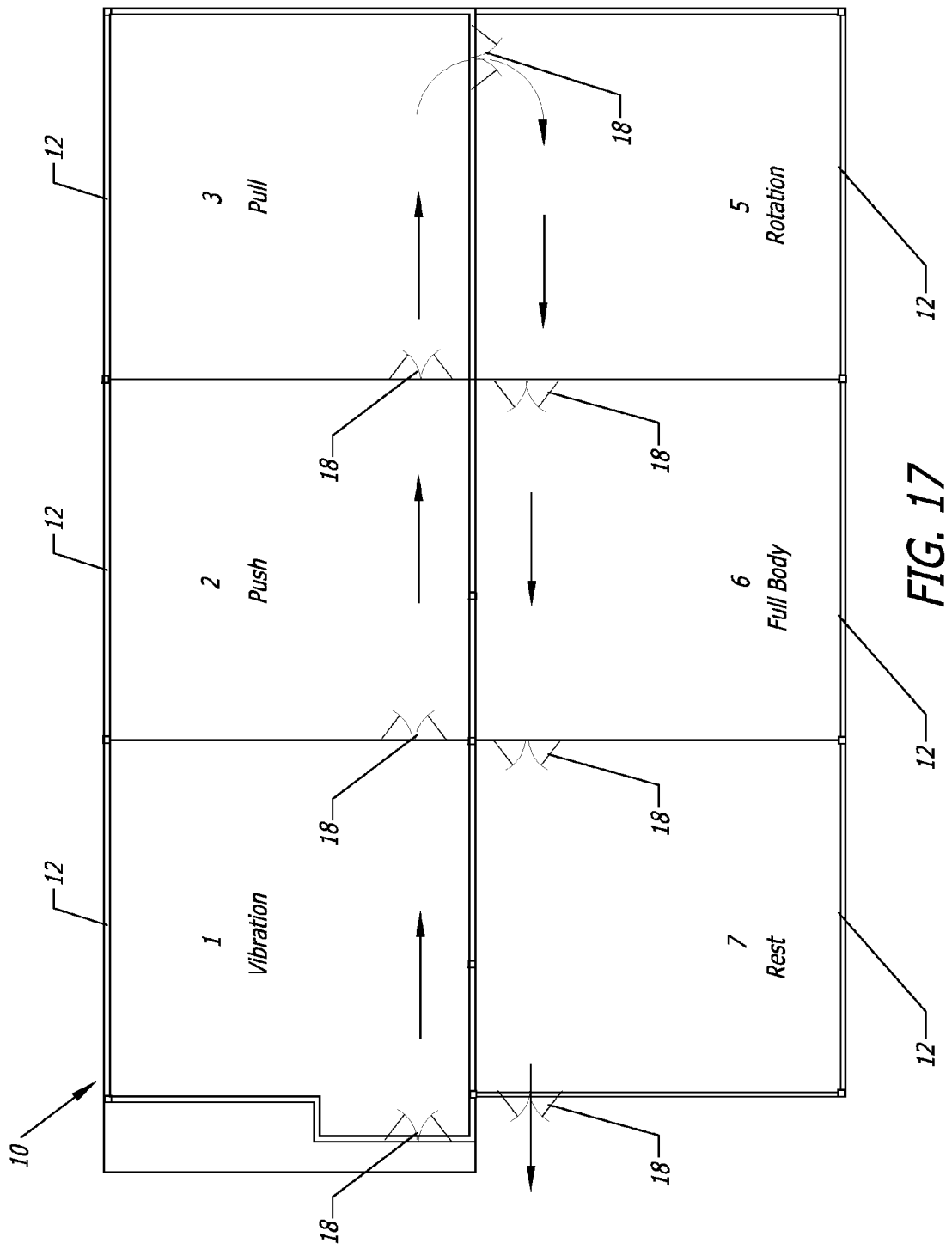
FIG. 17 is a diagrammatic view of a plurality of booths assigned an exercise, in accordance with the present invention.

With reference now to FIG. 17, an exercise facility or a section of an exercise facility or gym having fewer than the thirty booths could also be used to perform the exercise regimen. For example, a sequence of six booths could be used to perform the exercise regimen, the user performing the exercise regimen of FIG. 15 passing through each of the booths 12 five times in order to complete the entire thirty-sequence exercise regimen. Thus, the user could perform a sequence of exercises and continue to rotate through the booths 12 until the desired number of exercises or total exercise time has been achieved. It will be seen in FIG. 17 that each of the booths has been assigned a particular type of exercise corresponding to the exercise regimen of FIG. 15, such as "vibration", "push", "pull", etc. In such a case, the "vibration" booth could have a exercise device or machine which provides the vibration required, although the type of exercise performed in each pass through the booth could be different. Similarly, a different "push" or "pull" exercise could be performed in these booths by performing either a different manual exercise, or using the same piece of exercise equipment or machine to perform a different type of exercise. Of course, it is also contemplated that the same exercise using the same equipment be performed as the user passes through the booth multiple times throughout the exercise regimen. As such, it will be appreciated that the number of booths and the number of times or cycles that the user passes through the booth will depend upon the exercise regimen.

Figure 18:
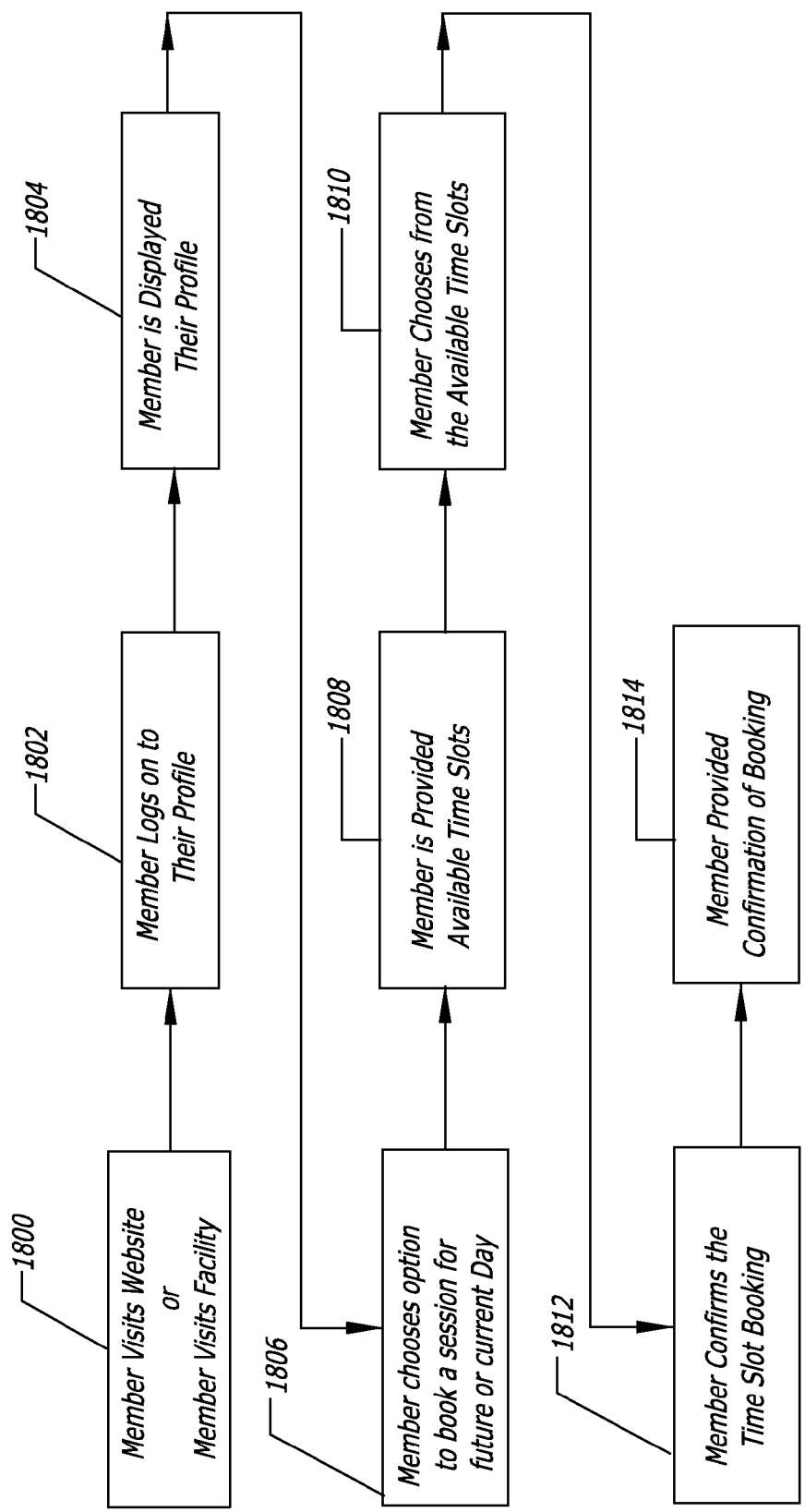
FIG. 18 is a flowchart depicting making reservations for the exercise facility of the present invention.

A user may simply show up at the exercise facility or gym and wait until a booth is available to enter into, typically the starting booth, or for the convenience of the user and to facilitate the scheduling of the booths, a reservation process is provided. With reference now to FIG. 18, the steps undertaken to reserve gym time is shown. The member visits the website or gym facility 1800. The member logs onto their profile which was provided during the registration process 1802. The member is displayed their profile 1804, and chooses an option to book a session for a future or current day 1806. The member is provided available time slots 1808 to begin his or her workout. The member chooses from the available time slots 1810. The member then confirms the time slot for booking 1812, and the member is provided confirmation of the booking 1814.

FIG. 19 illustrates exemplary members which have reserved and booked time slots. In the example provided in FIG. 19, members John, Tom and Jane start at booth 1 at 9:00 am, 9:01:20, and 9:02:40, respectively, thus being spaced from one another by one minute and twenty seconds. Assuming that the member is in each booth for a total time of one minute, this would provide twenty seconds for each member to input their results and move to the next booth after their exercise is completed in that booth. It will be appreciated that the time spent by each user within each booth exercising can be varied. For example, instead of one minute and twenty seconds, the actual time spent exercising in each booth may be two minutes, and only a ten second window to enter in the exercise results and move to the next booth may be provided, or other time variations. However, in order to keep the use of the booths synchronized and users flowing therethrough in an organized and controller manner, each user of each booth has the same amount of time to perform the exercise within that booth and move to the next booth.

Figure 20:
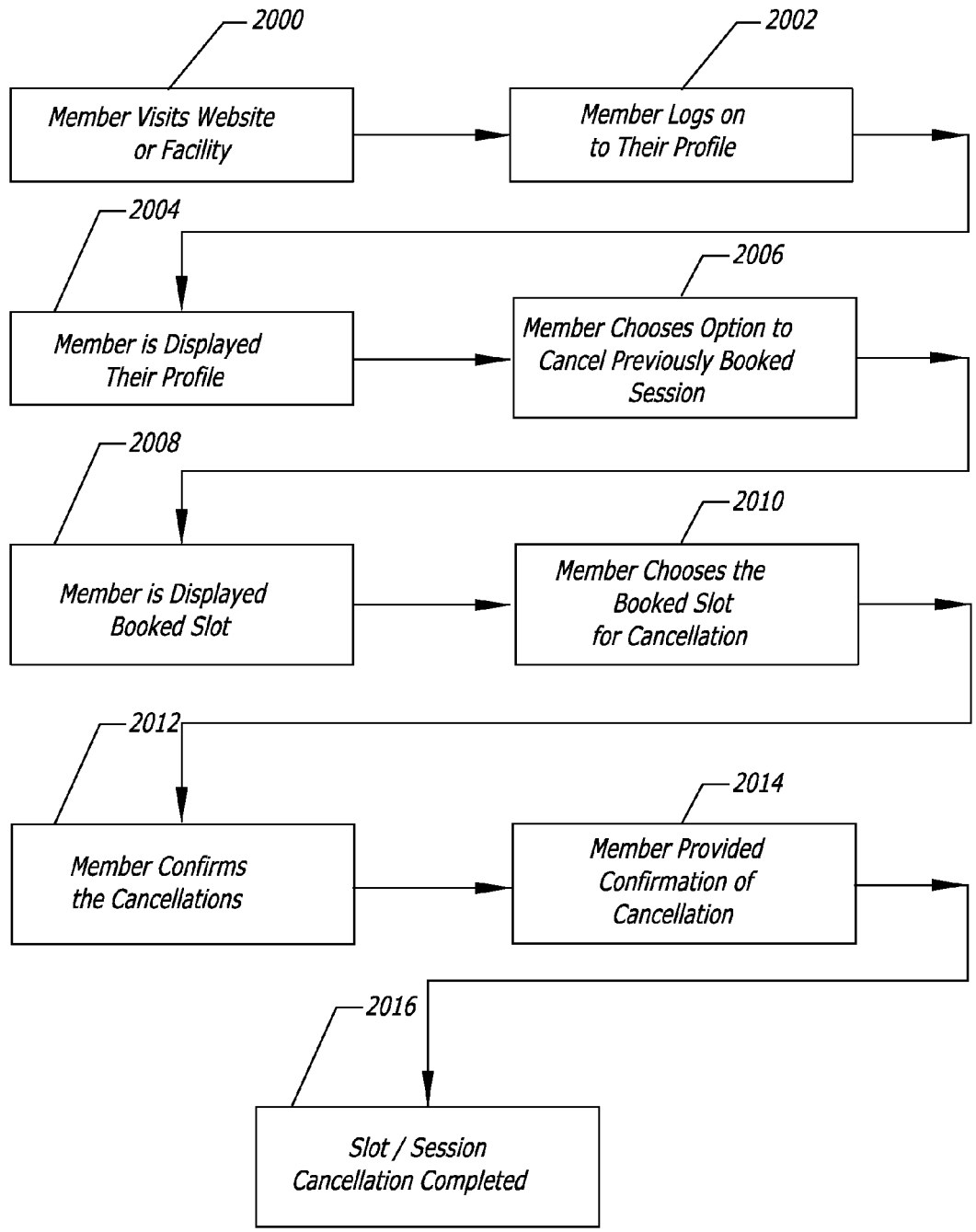
FIG. 20 is a flowchart depicting the steps taken in cancelling an exercise session using the present invention.

With reference now to FIG. 20, in order to cancel a previously-booked time slot, the member visits the website or gym facility 2000. The member logs on to their profile 2002 and after being displayed their profile 2004, chooses the option to cancel a previously-booked session 2006. The member is displayed the booked slot 2008, and chooses the booked slot for cancellation 2010. The member confirms the cancellation 2012, and is provided a confirmation of the cancellation 2014. The slot or session cancellation is then completed 2016, and the slot or session is made available by the system to other gym members.

Figure 21:
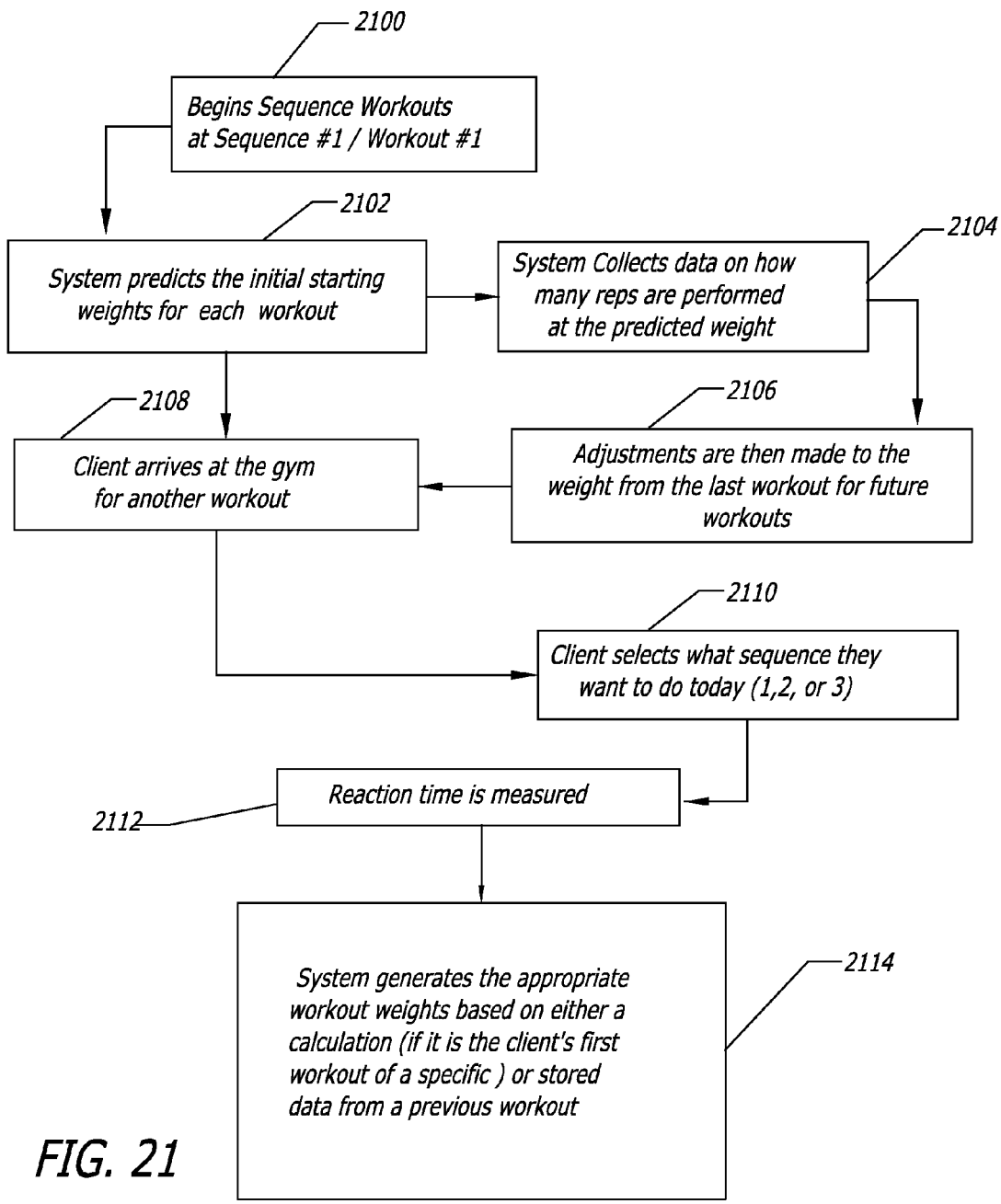
FIG. 21 is a flowchart depicting the steps taken in connection with automatically generating or modifying an exercise regimen for a user of the invention.
Figure 22:
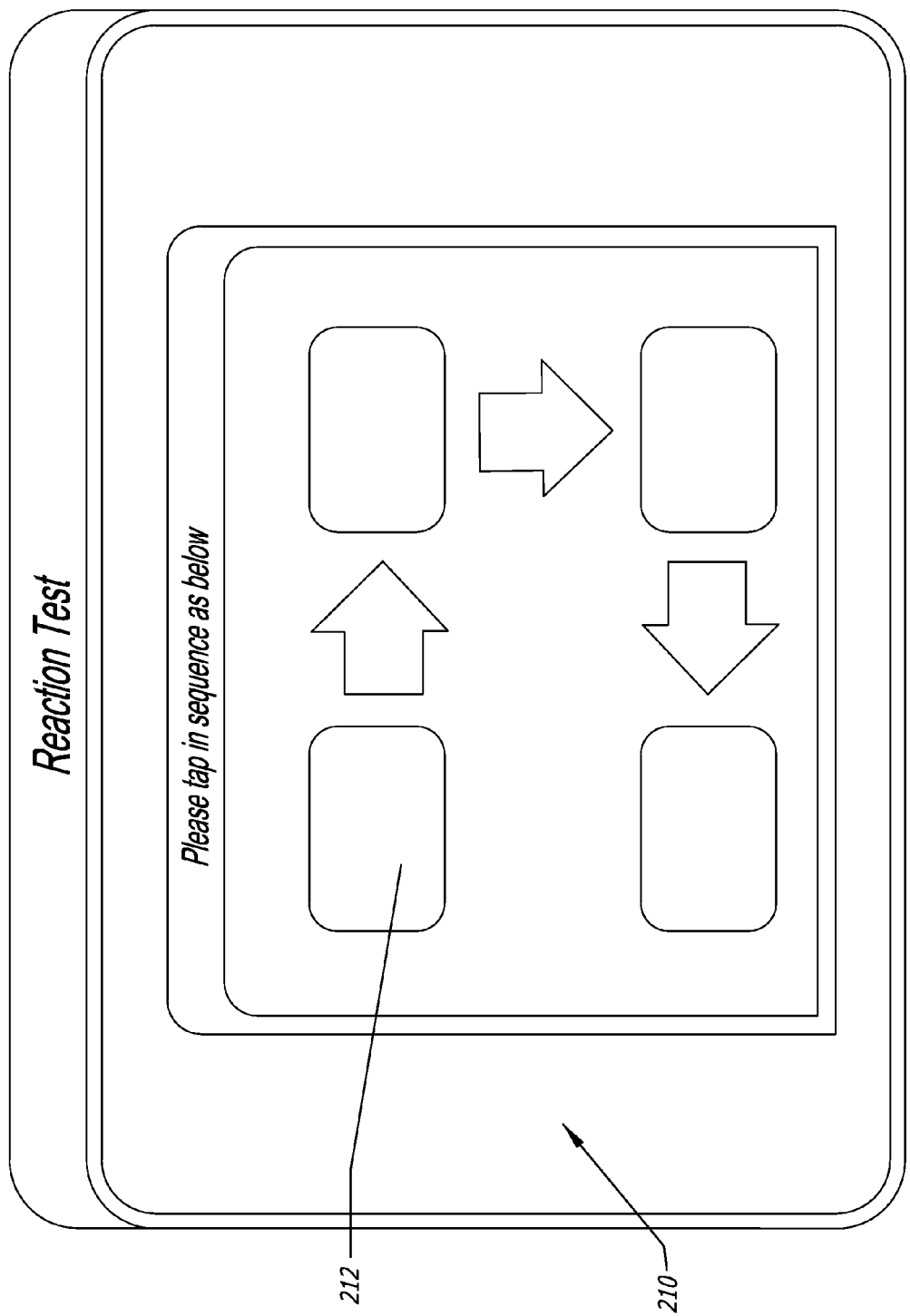
FIG. 22 is diagrammatic view of an electronic screen displaying a reaction test to be taken by the user prior to exercising.

With reference now to FIG. 21, when a new member registers as indicated above, the member may perform a grip strength test and/or a reaction test. With reference now to FIG. 22, an exemplary reaction test is shown, wherein an electronic display 210, such as a touch screen display, has a sequence of lighted icons 212. The user or member taps the sequence of the lighted icons 212 in a given order. If the user or member performs the reaction test relatively quickly, then an algorithm within the computerized system of the present invention determines that the user is relatively alert and in good health. However, if the time for performing the reaction test is relative slow, which could be due to the user having a lack of sleep, feeling ill, etc., an algorithm within the computerized system will detect this and depending upon predetermined parameters may adjust the user's personalized exercise regimen, such as lightening the weight or resistance of various exercises to be performed. Other types of reaction tests may be given to ascertain the mental and physical state of the user, or no reaction test may be given. The member may also be provided a selection of training programs, such as general fitness, strength, muscular endurance/toning, and weight management. The algorithms of the system will determine the amount of weight or resistance for each exercise depending upon the training or fitness program selected, user fitness test results, and user-related information provided during the registration process. For example, if the potential member is looking to add strength, the weight or resistance may be increased. However, if the potential member is looking for weight management or endurance, the weight or resistance may be lessened so that the user may perform a greater number of repetitions.

With continuing reference to FIG. 21, if the newly-registered member desires to work out that very moment, the system creates a sequence of workouts beginning with sequence number one, workout number one 2100. The system predicts the initial starting weights for the first of each workout 2102, depending upon the member's results of the grip strength test and reaction time, as well as the training program selected. The system then collects data on how many reps are performed at the predicted weight 2104 as the member completes a given workout and provides the input into the system. Adjustments are then made to the weight from the last workout for future workouts 2106, using a prediction equation within an algorithm of the software of the computerized system of the present invention. For example, if the user performs a certain number of repetitions at a given weight or resistance for a particular exercise and the number of repetitions dictates an increase in weight or resistance for that user the next time he or she performs the exercise, that user's personalized exercise regimen will be adjusted and updated accordingly in an automated fashion.

When the member arrives at the gym on another day for another workout 2108, the member may select which sequence they want to do that day 2110. The gym may be set up such that several sequences of booths are presented. For example, each sequence may include up to thirty booths, or will have a lower number of booths that may be repeated. Each sequence may be directed to and include different exercises or machines which can be used to exercise an individual in a distinct way as compared to the other sequences. For example, in sequence number one the exercises might be more tailored to emphasize a chest and back workout, whereas the exercises performed in sequence number two are biceps and triceps or leg intensive. Alternatively, each set of booths is directed to a different training or fitness program. A reaction test may be given 2112, and the system generates the appropriate workout weights based on either a calculation (if it is the member's first workout) or stored data from a previous workout 2114.

Figure 23:
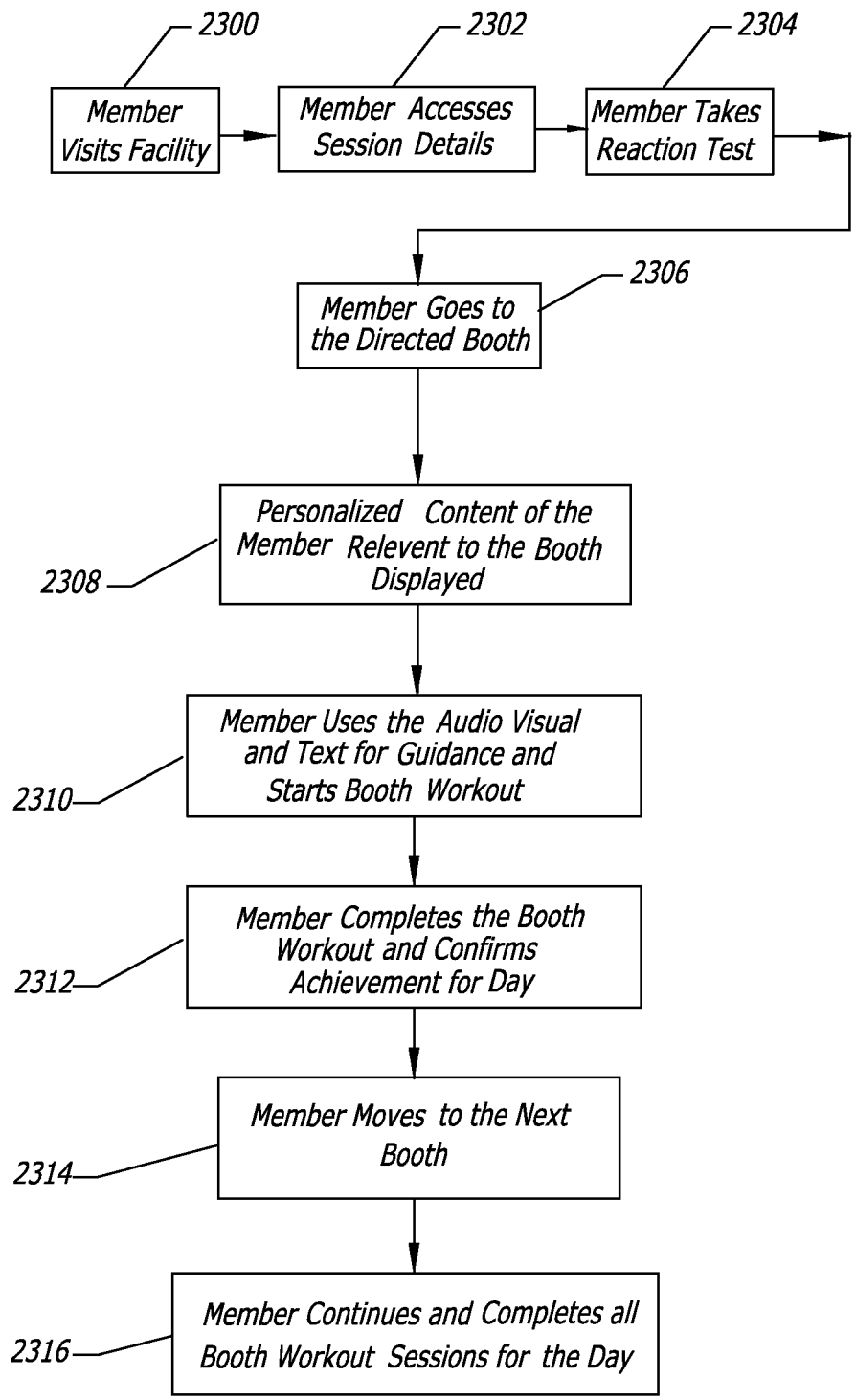
FIG. 23 is a flowchart depicting the steps taken in connection with a user or member being advanced through the booths of the present invention.
Figure 24:
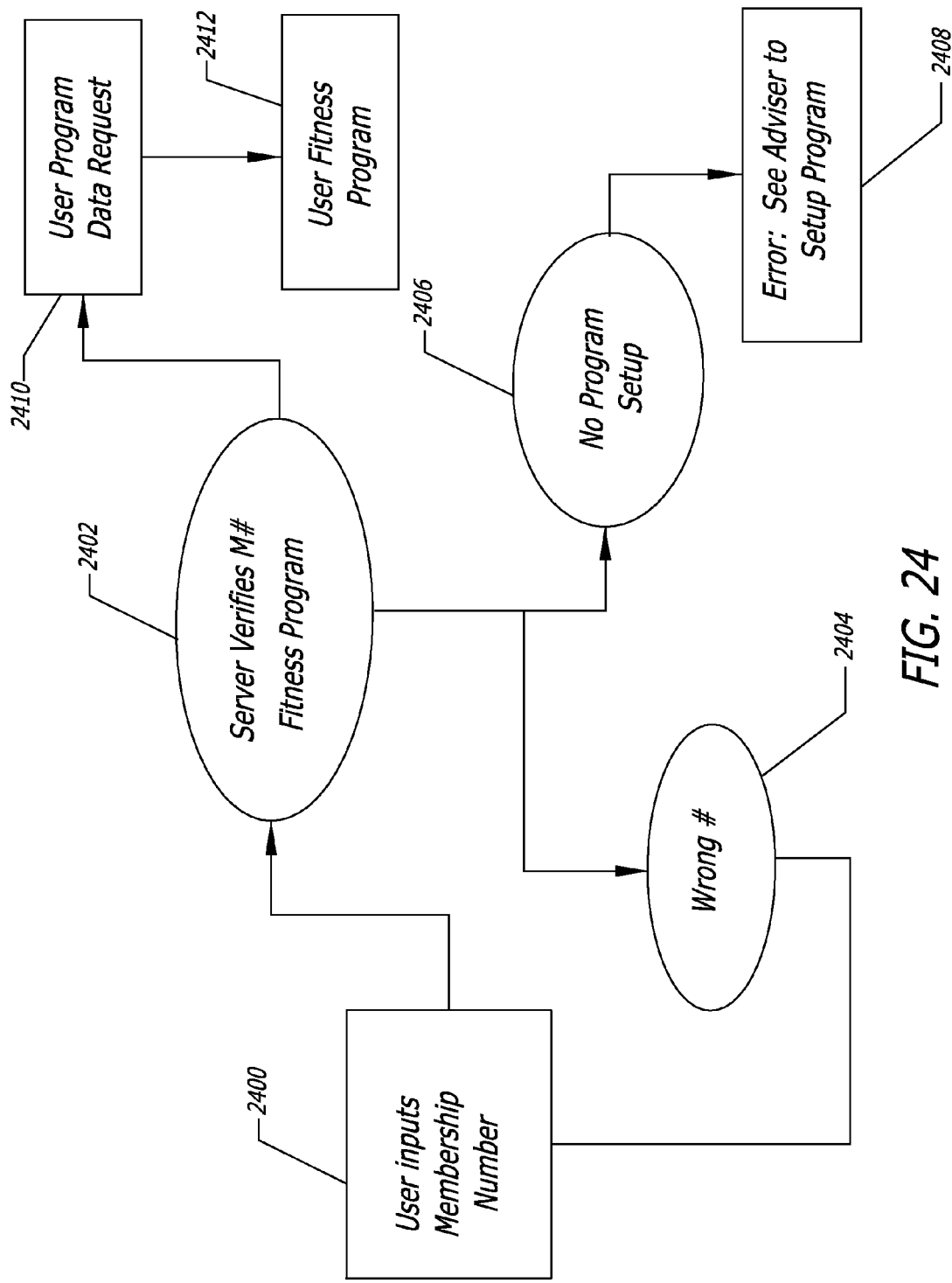
FIG. 24 is a flowchart depicting member log in, in accordance with the present invention.

With reference now to FIG. 23, when a member or user visits the exercise facility or gym for a workout 2300, the member accesses the session details 2302. With reference now to FIG. 24, this is done, for example, by the user inputting the user's membership number 2400. The server of the computerized system verifies the input number of the user and the fitness program 2402. If the membership number is not found, and is wrong 2404, the user is asked to input the membership number again. However, if the membership number is correct but there is no fitness program which has been set up 2406, the member or user is presented an error and asked to see an advisor to set up a fitness program, such as by completing registration, providing additional information to the registration process or the like. If the user's membership number is verified and a fitness program has been generated and established for that individual, the user's program data request 2410 is processed and the user is able to access their personalized fitness program 2412 and membership profile.

The steps taken in accordance with FIG. 24 may be done in a variety of ways. For example, the user may enter his or her membership number or code or user name and password into a touch screen display, computer, kiosk or the like within the lobby of the gym. Alternatively, the user may have a card or other electronic device which is electronically read or electronically transmits the user's membership number, code, etc.

However, in one embodiment of the invention, as illustrated herein, each user or member visiting the exercise facility is either provided a handheld electronic device, such as a tablet, or the user brings in his or her handheld electronic device, such as a cell phone, electronic tablet, or the like. Such handheld electronic devices 250 will include an electronic display screen 252 capable of displaying relevant information pertaining to the user and his or her exercise regimen. The handheld electronic device will also have means of inputting data into the device, such as a touch screen, a virtual keyboard, a physical keyboard, etc. In one embodiment, the handheld device 250 is in electronic communication, such as via Bluetooth or other wireless network, to the computerized system of the invention, such as a local server at the exercise facility, a remote server, such as in the cloud, or the like.

Figure 25:
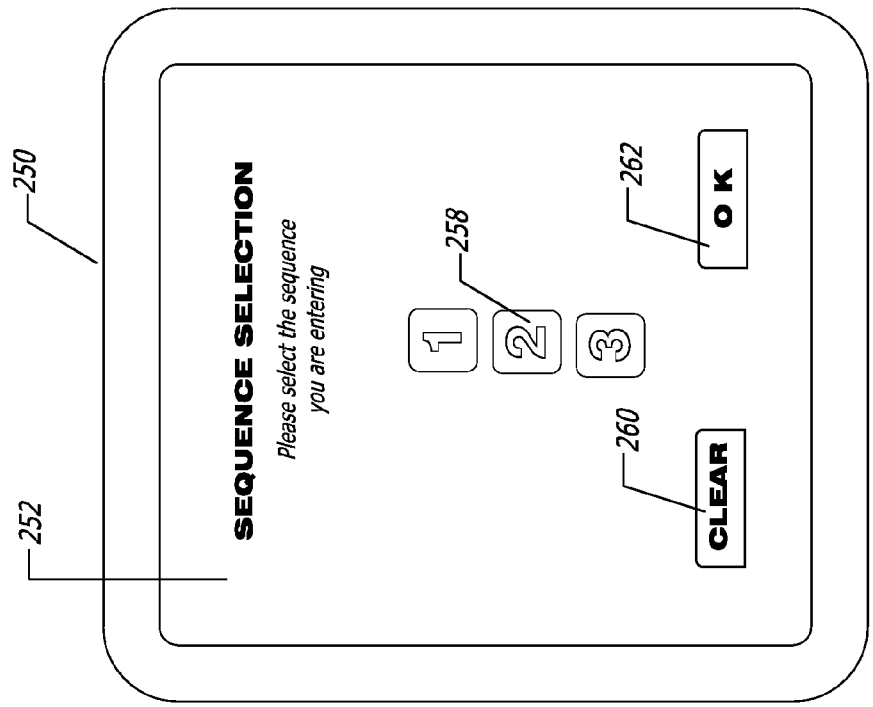
FIG. 25 is a diagrammatic illustration depicting an electronic display screen for entering a user's membership identification.

With reference now to FIG. 25, the user utilizes the handheld electronic device 250 to enter in the user's membership identification and PIN into the designated windows, such as the illustrated windows 254 and 256. This may be done using the keys of an electronic and virtual keypad 258, via a touch screen. Additional buttons may be incorporated such as a button 260 to clear inputted information or a button 262 to enter or approve information.

Figure 26:
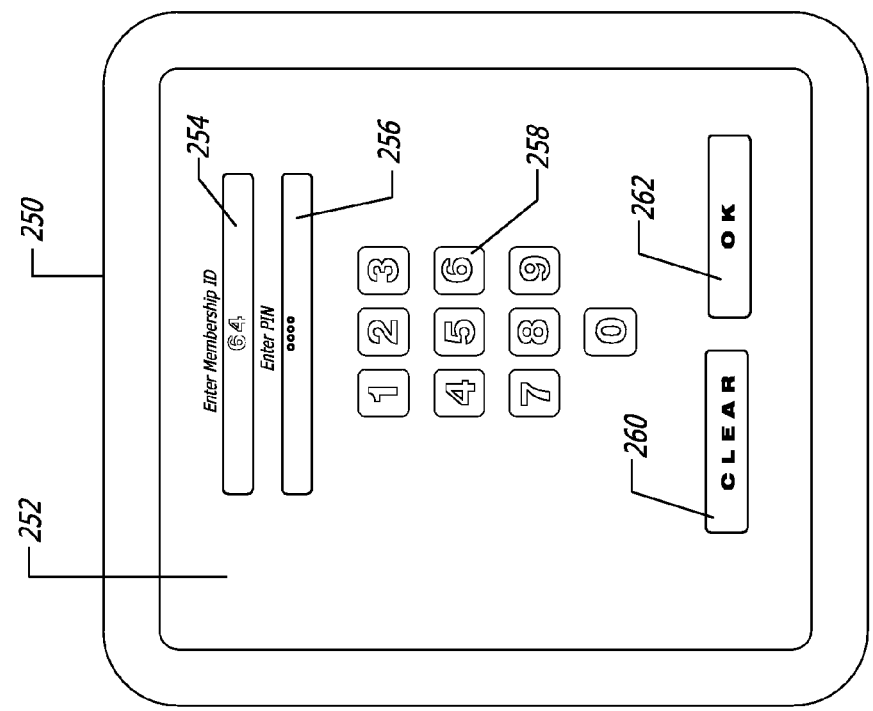
FIG. 26 is a diagrammatic view of an electronic screen of a handheld electronic device illustrating a sequence selection, in accordance with the present invention.

Once the user's membership information is input, and accepted, as shown in previously discussed FIG. 24, the user may be presented an option to select an exercise sequence, as illustrated in FIG. 26. This may be the case, for example, if the exercise facility has multiple sets of sequenced booths. For example, the exercise facility may have three sets of thirty exercise booths. Alternatively, the exercise facility may have a number of sequences of a smaller number of booths, such as four sets of booths, each set having a sequence of six booths each. The user may select a sequence which contains exercise equipment or exercises which the user prefers, or in order to add variety to the user's exercise regimen. It is also contemplated by the present invention that an exercise facility has a single set of exercise booths, for example thirty booths, each booth having the necessary exercise equipment therein, but the computer software is capable of providing a varied workout session by varying the exercises to be performed in each booth, even if the same exercise equipment is used.

Figure 27:
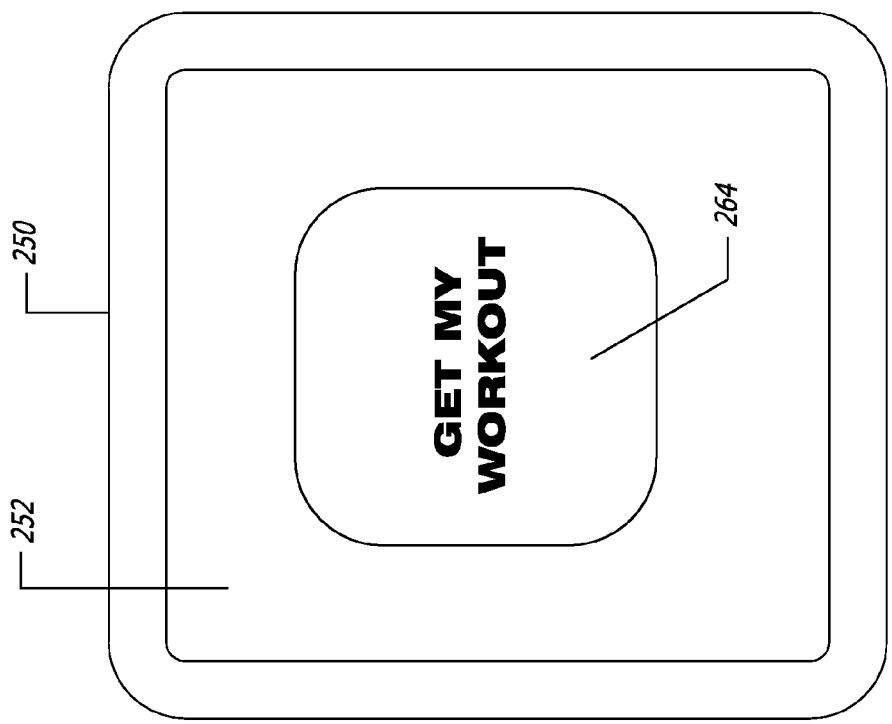
FIG. 27 is a electronic screen of a handheld device displaying the option to obtain and download an exercise regimen workout, in accordance with the present invention.

With reference now to FIG. 27, after logging in and selecting a sequence, if applicable, the user is able to request the download of his or her exercise workout session or regimen to be performed that day, such as by depressing or otherwise selecting a button, such as labeled "get my workout". Typically, the handheld device 250 has a software application downloaded thereto which supports the present invention. The software application may be used to enter membership identification, membership profile information, etc. and communicate directly with the computerized system, such as a local or central server, to obtain information, receive updated workout sessions and regimens, upload user performance data and the like. Thus, the user upon entering the exercise facility will open the software application on his or her phone, tablet, or other handheld electronic device, such as one provided by the exercise facility. The software application will walk the user through the steps in an easy and convenient manner.

Referring again to FIG. 23, as described above, the user or member may take a reaction test 2304. An exemplary reaction test was discussed above in connection with FIG. 22. The reaction test may be used to determine the amount of fatigue and mental clarity that the individual is experiencing on any particular day. It has been found that individuals have variations from day-to-day as to their ability to complete a workout regimen. For example, the individual might be tired due to lack of sleep, illness, etc. which can adversely affect the individual's ability to complete the workout regimen. The present invention may take such variations into account by having the individual perform a reaction test before the workout session is started. The results of the reaction test will give an indication of the mental and physical alertness and well-being of the individual that particular day, and the algorithms of the present invention will adjust the weight or resistance to be performed for the exercises of the workout regimen that day based on predetermined reaction test result parameters. The reaction test can be as simple as selecting a sequence of lights presented on a touch screen display, and measuring the reaction time between the lighting of the object and the member pressing the object. The reaction test may be performed multiple times and the user's reaction times averaged. Such a reaction test may be performed on the handheld device, with the results communicated, typically wirelessly, to the local or remote server of the computerized system, or analyzed via the downloaded computer software application on the handheld device. Alternatively, a dedicated device or display screen or the like within the exercise facility may be used to administer the reaction test.

Figure 28:
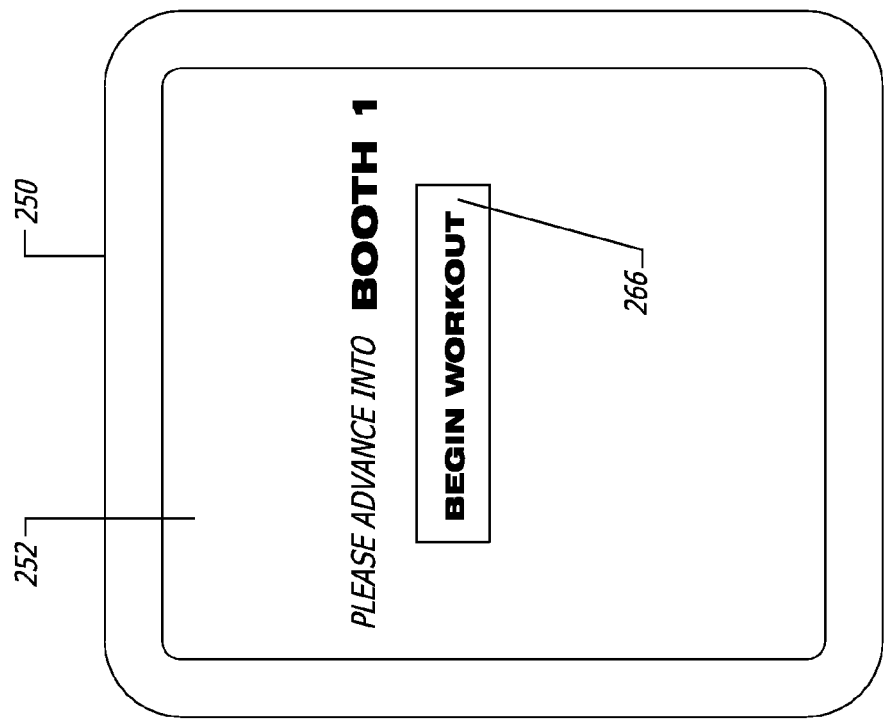
FIG. 28 is an electronic screen of a handheld device displaying notification to advance into a booth and begin the workout session, in accordance with the present invention.

The member is then directed to go into a particular booth 2306. As illustrated in FIG. 28, the display screen 252 of the handheld device 250 may present a message to the user to advance into a particular booth to begin the user's workout. There are various ways and mechanisms in which the sequencing of the user into the booth may be performed. For example, if the user has previously registered a booth for a particular time, then that user will enter that booth at that time. Alternatively, an audio or visual indicator may indicate when that particular booth is open and available for the user to enter into to begin his or her exercise within that booth and the workout session for the day. An audio notification system may be used for each set of booths or even the entire exercise facility so as to indicate when the users are to advance from booth to booth. For example, periodically, such as every minute or two, a voice may be broadcast indicating that the exercise is to be stopped and the results entered, with a provision of a predetermined amount of time, such as ten or twenty seconds, for the user to do so. Then a verbal countdown may be broadcast such as five, four, three, two, one, advance in order to alert each individual in each booth to advance to the next booth. At this time, the individual entering the initial or first booth would enter into that booth to begin the workout session.

The workout program consists of a given number of exercises performed over a given period of time. These exercises typically involve a piece of exercise equipment or machine but can involve a manual exercise, such as sit-ups, push-ups or the like. The system of the present invention automatically generates the workout program for that individual on that particular day based upon the aforementioned tests and the number of repetitions entered into the system at each exercise station by the user. Each exercise is timed and the user provides data input as to the progress made during each exercise, such as entering the number of repetitions of the exercise performed. For example, if the individual is able to perform eighteen push-ups during the one-minute interval allotted, the individual will input this number of repetitions electronically into the system. The user will then move to another exercise station, such as a piece of equipment or machine in which the user is to curl a given amount of weight.

Each member of the gym will begin at an assigned booth number. Each booth will be assigned a particular stretch, warm-up, exercise or rest period in accordance with the exercise sequence generated for the user of the computerized system. The individual will proceed from booth to booth, as directed by the computerized system, thus obtaining an optimum workout without having to worry about which exercise to perform next, what the individual's performance results were for that exercise in a previous workout session, or how much additional weight or how many additional reps should be done by that individual for that exercise. The computerized system has algorithms which tracks the input, typically merely the entry of the number of repetitions, by the member from exercise to exercise and workout session to workout session and automatically alters the workout regimen for that individual. Thus, for example, if the computer program, based upon prior entered information, determines or predicts that the individual should be performing ten repetitions of twenty pounds, but that individual can in fact perform twenty-five repetitions, the computer program will adjust the workout regimen for the individual at the next workout session such that either additional weight and/or additional repetitions will be part of the exercise regimen for that individual.

This happens behind the scenes as the gym member merely enters the assigned booth and is instructed by the system, such as via the screen display, the exercise to be performed, the weight or resistance to be used, and the time in which to perform the exercises. The system will prompt the member at the end of the allotted time to input the number of repetitions performed. The system will then prompt the member to move to the next booth for the next exercise, or possibly a rest period.

The present invention contemplates a full body exercise by varying the exercises to be performed with arm muscle groups, chest and back muscle groups, core muscle groups, and leg muscle groups. Cardiovascular exercises are also contemplated by the invention. By varying the type and number of exercises, a full body workout can be obtained in a relatively short period of time, such as within thirty minutes.

It is also within the scope of the present invention that a series of booths be specialized so as to create a cardiovascular workout, an upper body workout, a lower body workout, etc. to provide the gym member the flexibility in choosing to focus on these types of exercises. This would entail having multiple series or sequences of booths which are independent of one another. For example, three sets of thirty booths could comprise three sequences, each sequence providing approximately a thirty minute workout. Exemplary exercise programs which can be created by sets of booths and selected by the user or gym member include a general fitness program, a weight management program, a strength enhancing program, a muscle toning program, and a muscle endurance program. A particular set of booths may have exercise equipment or exercises assigned thereto which are more specific or applicable to a given desired fitness program. Alternatively, or in addition to, the automatically generated workout regimen created by the computerized system could account for the desired and selected fitness program so as to alter the weight or resistance, number or repetitions or the like of each exercise to be performed. For example, the number of repetitions at a given weight may be increased for a muscle endurance program, whereas the amount of resistance or weight would be increased for a strength enhancing program of a given exercise.

With reference now to FIG. 28, once the user or member enters the first designated booth, according to time, visual or audible notification, etc., the user will select a button 266 in order to begin the workout. As described above, the workout regimen and session for that day will have been downloaded to the user's handheld electronic device 250 from a server or computer of the computerized system.

Figure 29:
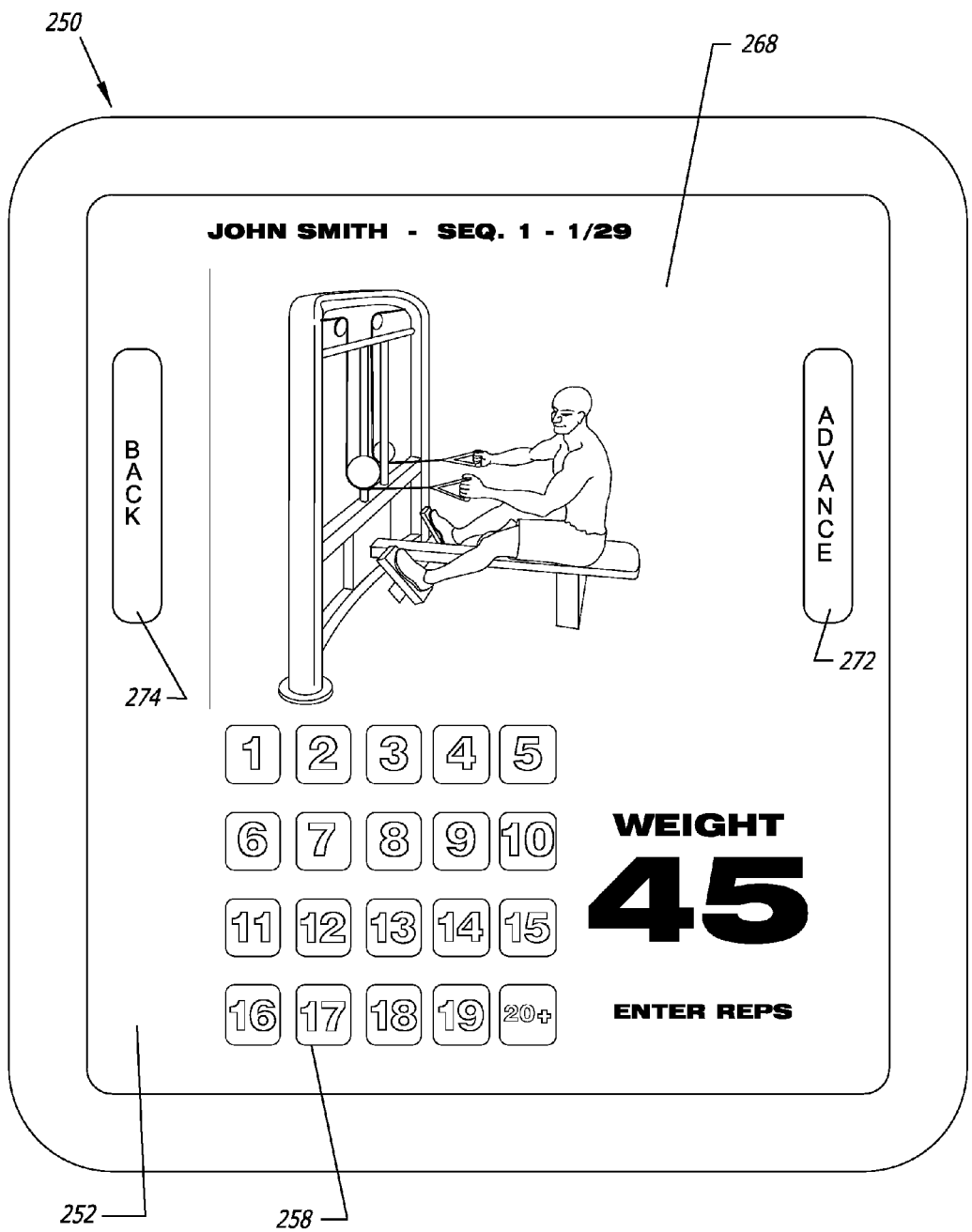
FIG. 29 is a diagrammatic view illustrating a handheld electronic device with a screen providing a tutorial of an exercise to be performed in a booth and a virtual keyboard for entering a number of repetitions, in accordance with the present invention.

Referring again to FIG. 23, the personalized content of the member relevant to the booth is displayed 2308, and the member uses the audio/visual and text for guidance and starts the booth workout 2310. This is graphically illustrated in FIGS. 29 and 30. On the display screen 252 of the electronic device 250, a window 268 is provided having video, animation, photographs, or the like which provides a tutorial and shows the user how to perform the exercise for that booth. This may include illustrations and/or text messages on how to adjust the equipment to fit the size of the user and the predetermined weight or resistance, and then how to perform the exercise. As illustrated in FIG. 29, the display screen may also display the name or identification of the user, the sequence selected, and the current booth in which the user is to exercise, as well as the total number of booths.

Figure 30:
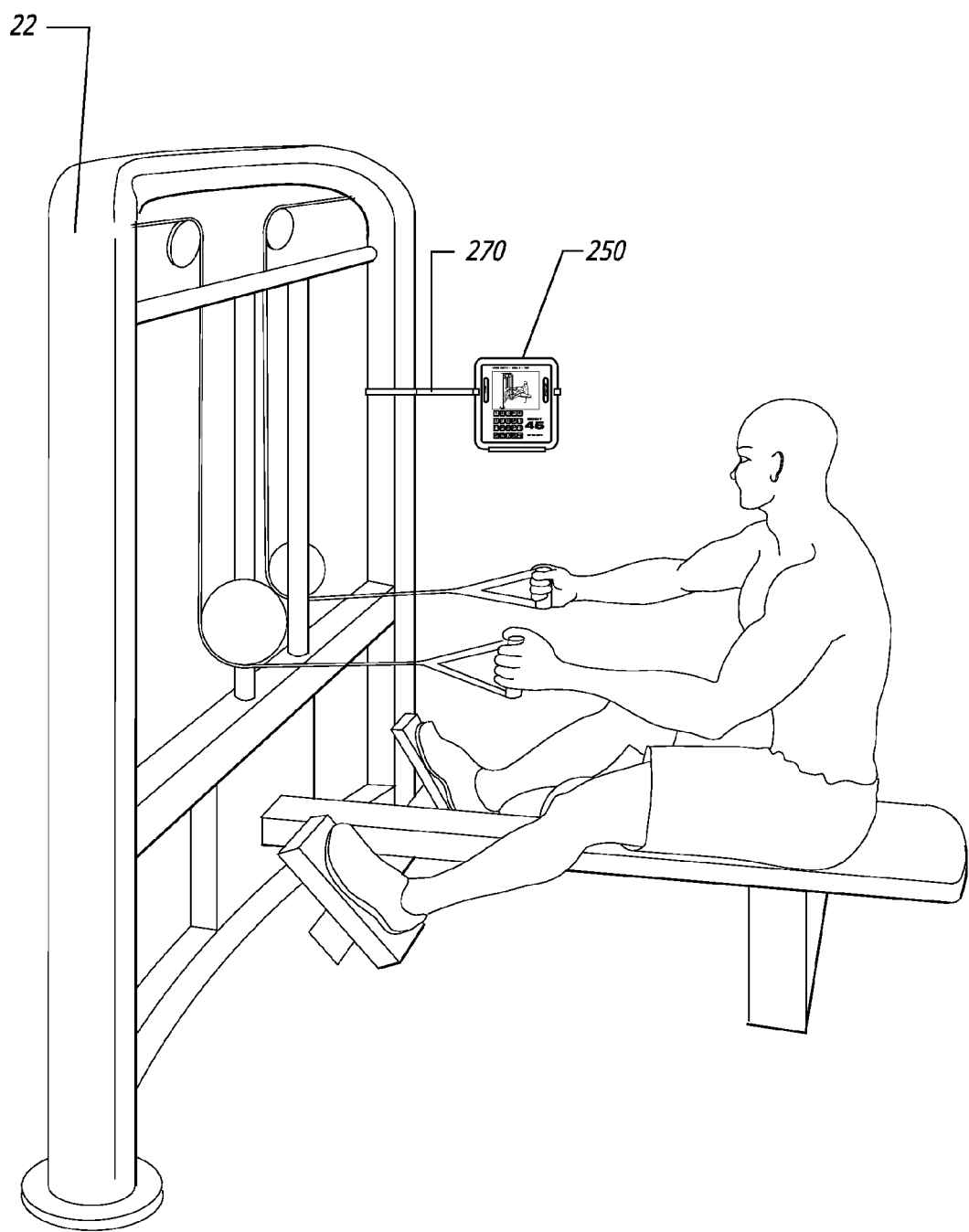
FIG. 30 is a diagrammatic view of a user exercising while viewing the display screen of the handheld electronic device, in accordance with the present invention.

With reference now to FIG. 30, it is contemplated by the present invention that a stand or holder 270 be provided within the booth, and possibly attached to or extending from the exercise equipment 22 which will hold the handheld device 250 in such a manner so as to be viewable by the user performing the exercise so that the user or member may be able to ensure that they are performing the exercise correctly.

Referring again to FIG. 29, as indicated above, typically within at least some of the booths a predetermined resistance or weight to be used by the user during the exercise is indicated. For example, in FIG. 29 the user is to perform as many repetitions as possible within the allotted time of forty-five pounds. The user will perform as many repetitions of the exercise at forty-five pounds within the allotted time given, such as thirty seconds, one minute, two minutes, etc. When a notification is received that the allotted time is up, such as either via a timer through the handheld electronic device 250 or a central visual and/or audio notification for the set of booths or the exercise facility, the user stops the particular exercise.

Referring again to FIG. 23, the member completes the booth workout and confirms the achievement or performance for the day 2312. The member then moves to the next booth 2314, and continues and completes all the booth workout sessions for the day 2316.

Referring again to FIG. 29, in the event that the particular exercise requests a number of repetitions that were performed to be entered, the user does so, such as via a virtual keypad 258, as shown. The user will then advance to the next booth, and may select a "advance" button 272 or the like to indicate to the software that the user has completed that particular exercise and the software then presents a screen displaying the information relating to the next booth, such as that illustrated in FIG. 31. A "back" button 274 or the like may be provided so that the user may go back to the previous screen, such as if an error was made or the like.

Figure 31:
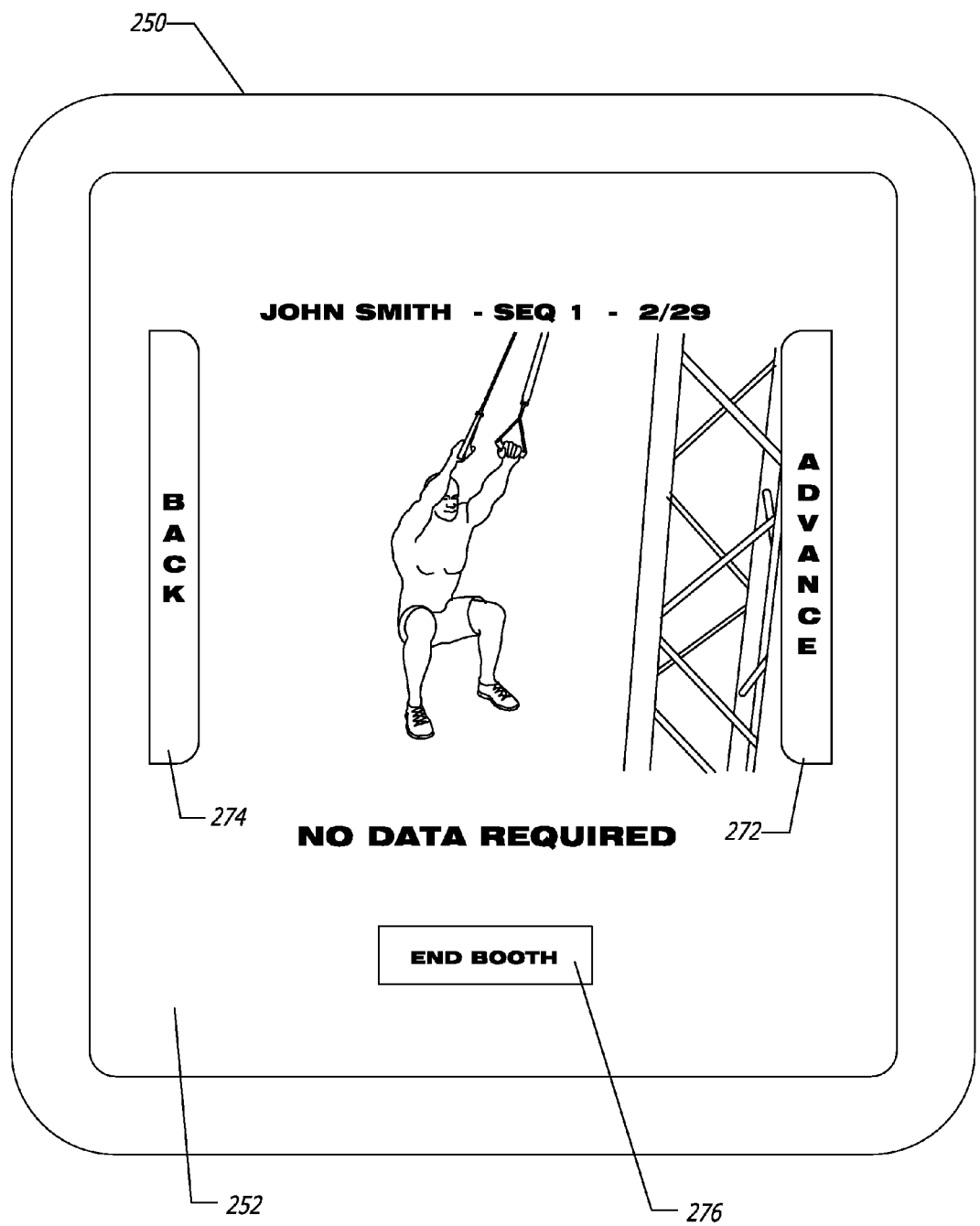
FIGS. 31-36 are diagrammatic views of an electronic screen of a handheld device displaying electronic pages directed to various exercises to be performed in different booths of the user's exercise regimen, in accordance with the present invention.

With reference to FIG. 31, although a piece of exercise machinery or an exercise device may be placed within each booth which will have an adjustable resistance or weight, it is contemplated by the present invention that in other booths exercise equipment may be provided which does not require adjustment of resistance, weight, etc. It is also contemplated that no exercise equipment be provided in certain booths and instead merely an appropriate surface, such as a mat, be provided so that the user may perform the necessary stretches, calisthenics, pushups, sit ups, or the like. It is also contemplated that exercise equipment provided within the booths be multipurpose such that multiple, different exercises may be performed utilizing the same exercise equipment.

With reference again to FIG. 31, an exercise is illustrated which includes handles and resistance bands which extend from a framework and which are manipulated in such a way so as to perform the exercise. In this case, the user performs the exercise over the allotted period of time, but does not enter in any number of repetitions as there would be no future change to the resistance or weight or the like for this exercise. Instead, at the end of the allotted time, the user may select an end booth button 276 or the like, or merely the advance 272 button or the like to move on to the next exercise.

Figure 32:
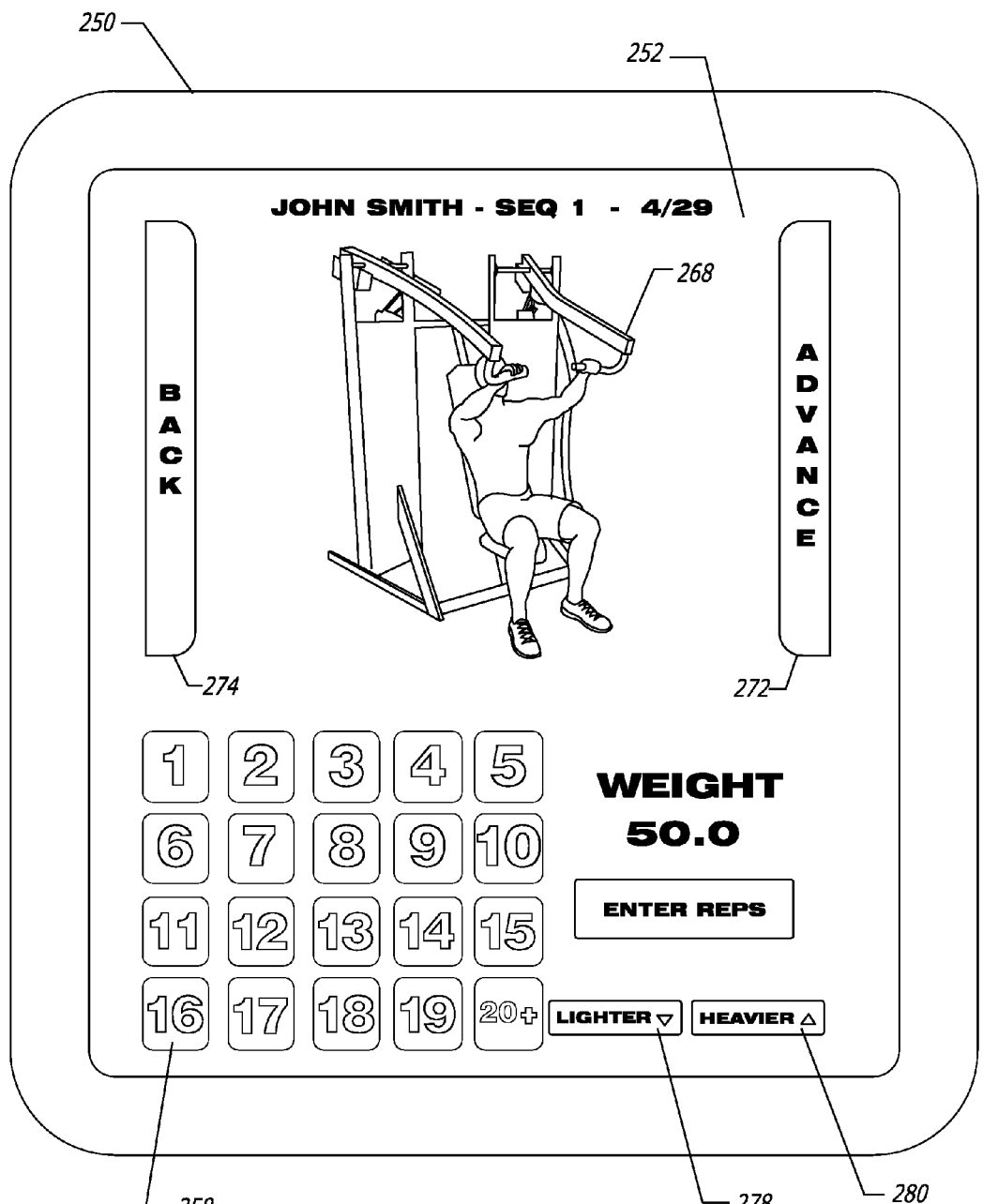

With reference now to FIG. 32, yet another booth having a different piece of exercise equipment therein is shown as part of the user's exercise regimen for that particular day. It is contemplated by the present invention that the user may be able to manually indicate whether the weight or resistance should be decreased or increased, such as by selecting a "lighter" button 278 or "heavier" button 280, which manual indication will be considered by the algorithm when adjusting the user's personalized workout regimen for a future workout session.

Figure 33:
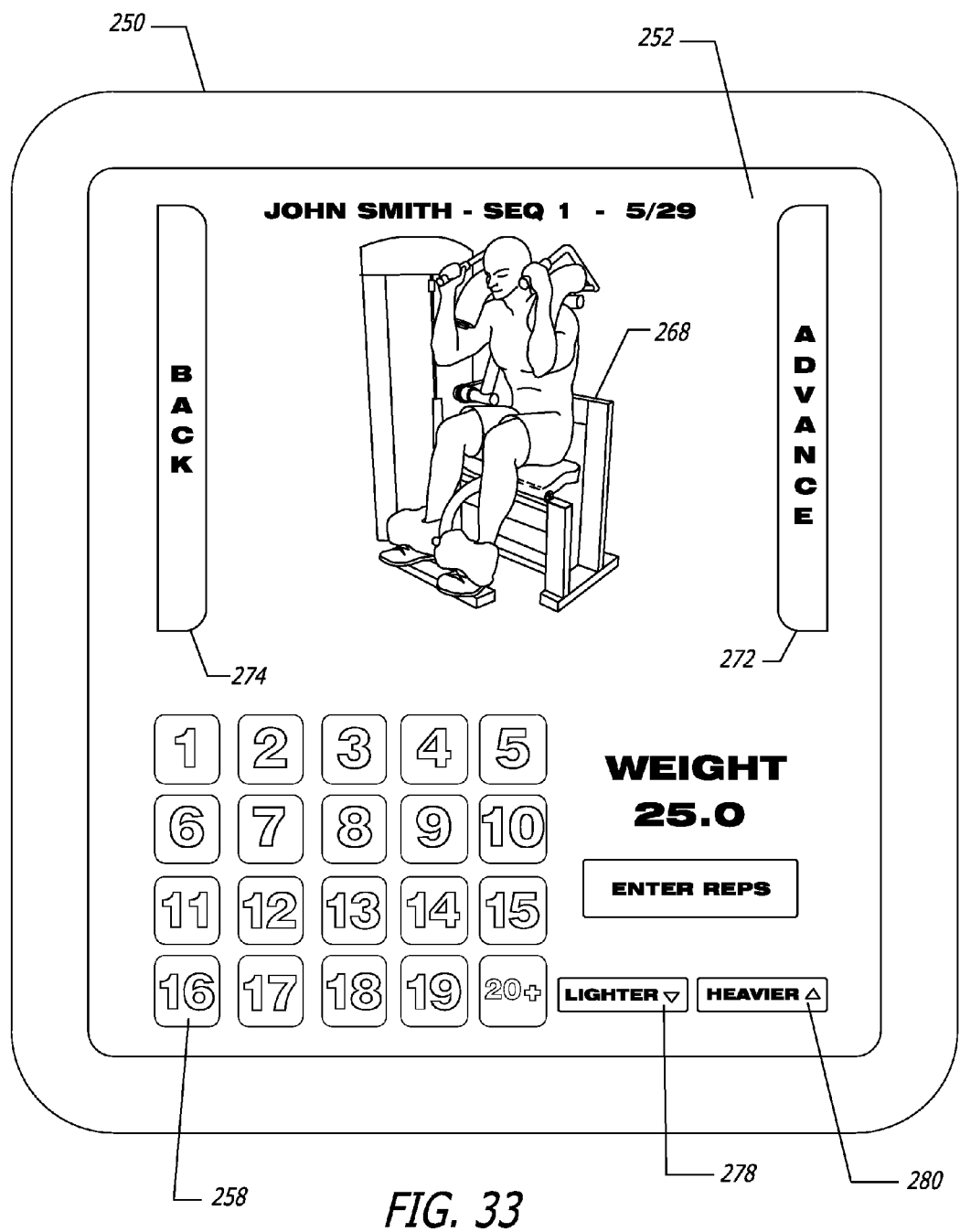

FIG. 33 shows yet another screen for another booth, containing a different piece of exercise equipment to perform a different exercise, in accordance with the present invention. The user performs this exercise, as shown in the tutorial 268 for the allotted time and then enters in the number of repetitions after the allotted time expires.

Figure 34:
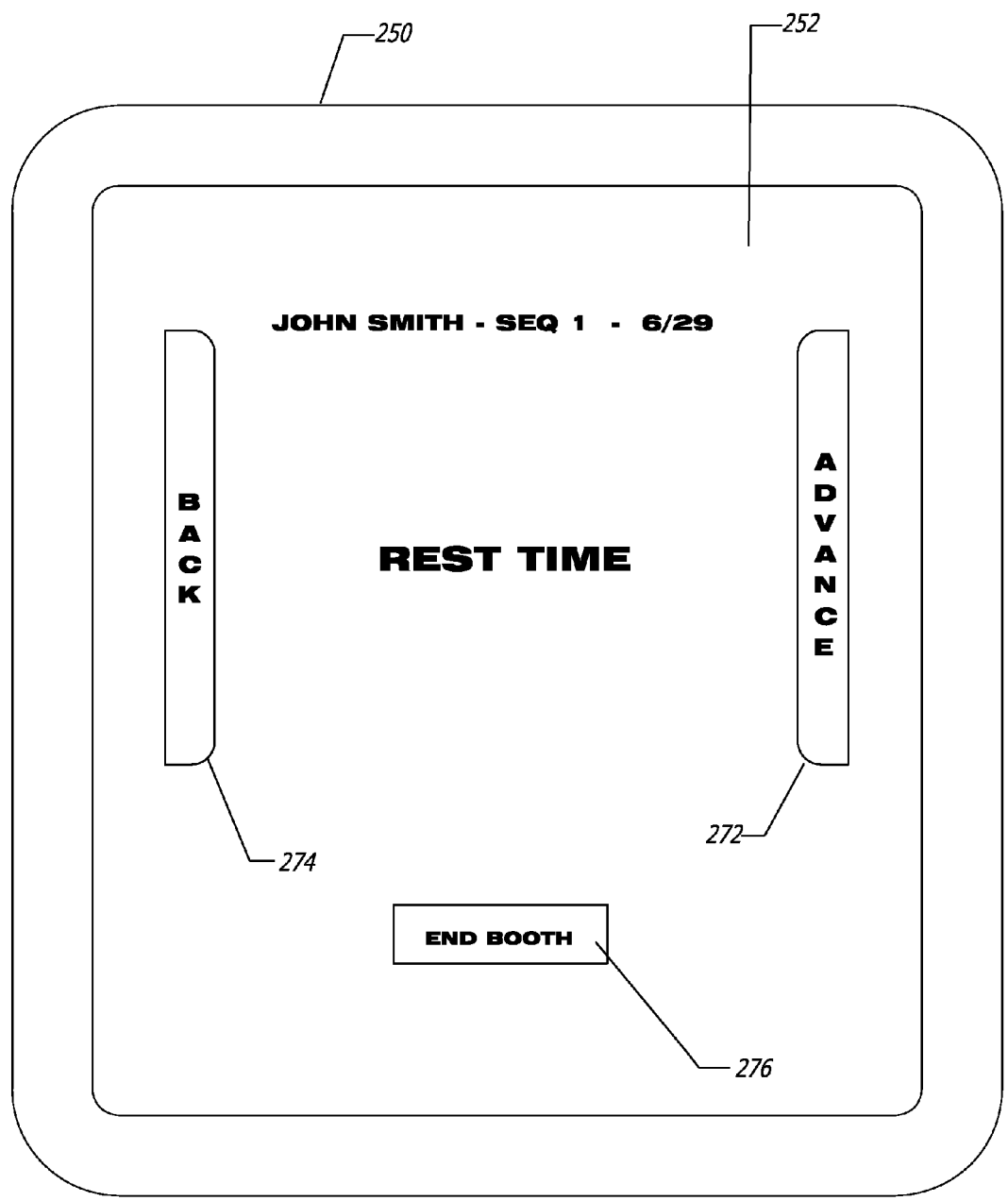

With reference to FIG. 34, it is contemplated by the present invention that there be rest periods of time interspersed throughout the workout session. These may be inserted, for example, after every four or five exercises, ten exercises, or not at all. In the case of a rest time, the user will simply rest in a dedicated rest booth, in a hallway, or the like for the allotted period of time before proceeding to the next booth and exercise. During this time, it is contemplated by the present invention that the user will be able to access reports through the software application showing the user's workout performance history for that day, comparisons of past workout performance, goals, etc. Alternatively, the user may simply access multimedia, listen to music, or do nothing and merely rest for the allotted period of time.

Figure 35:
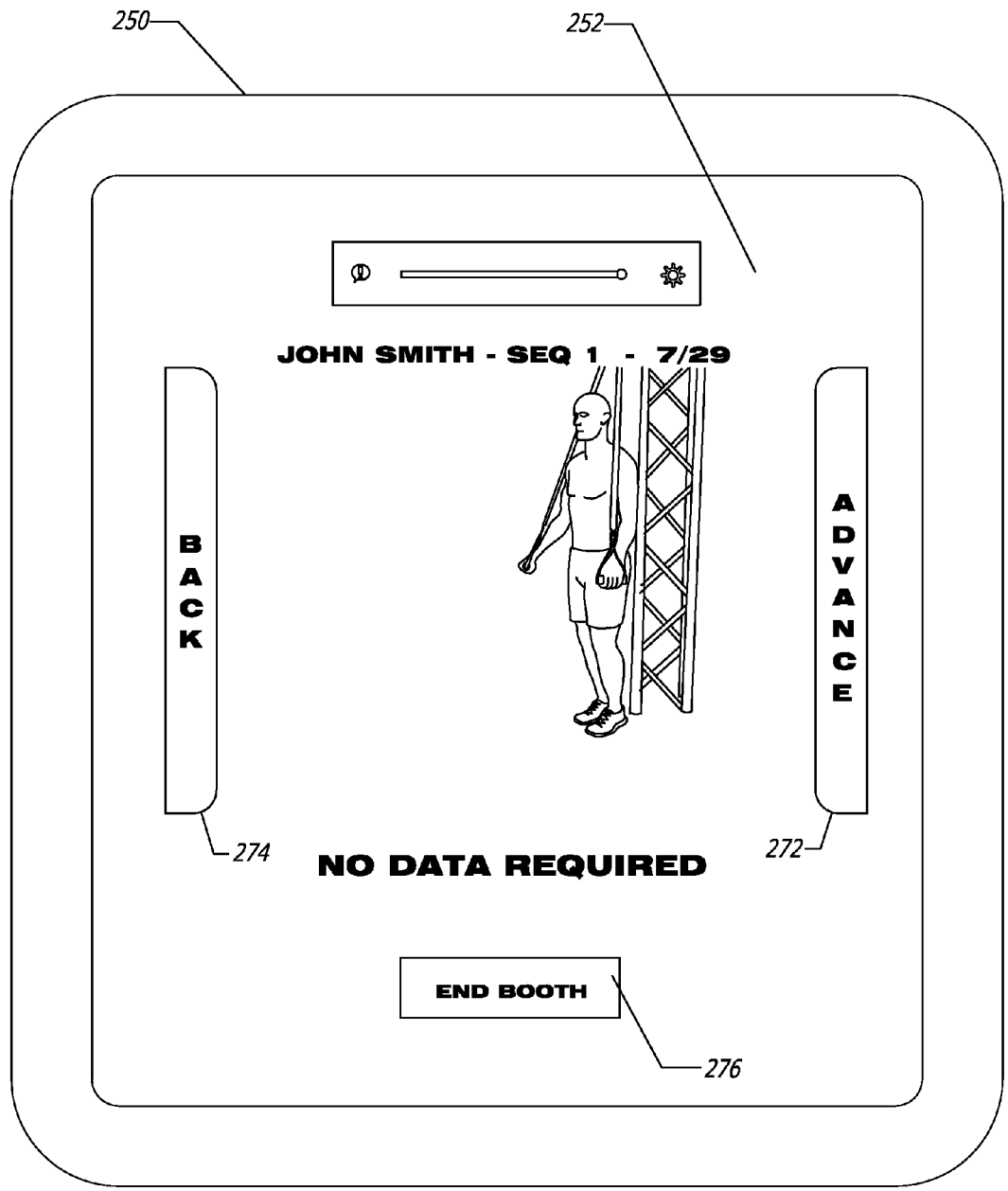
Figure 36:
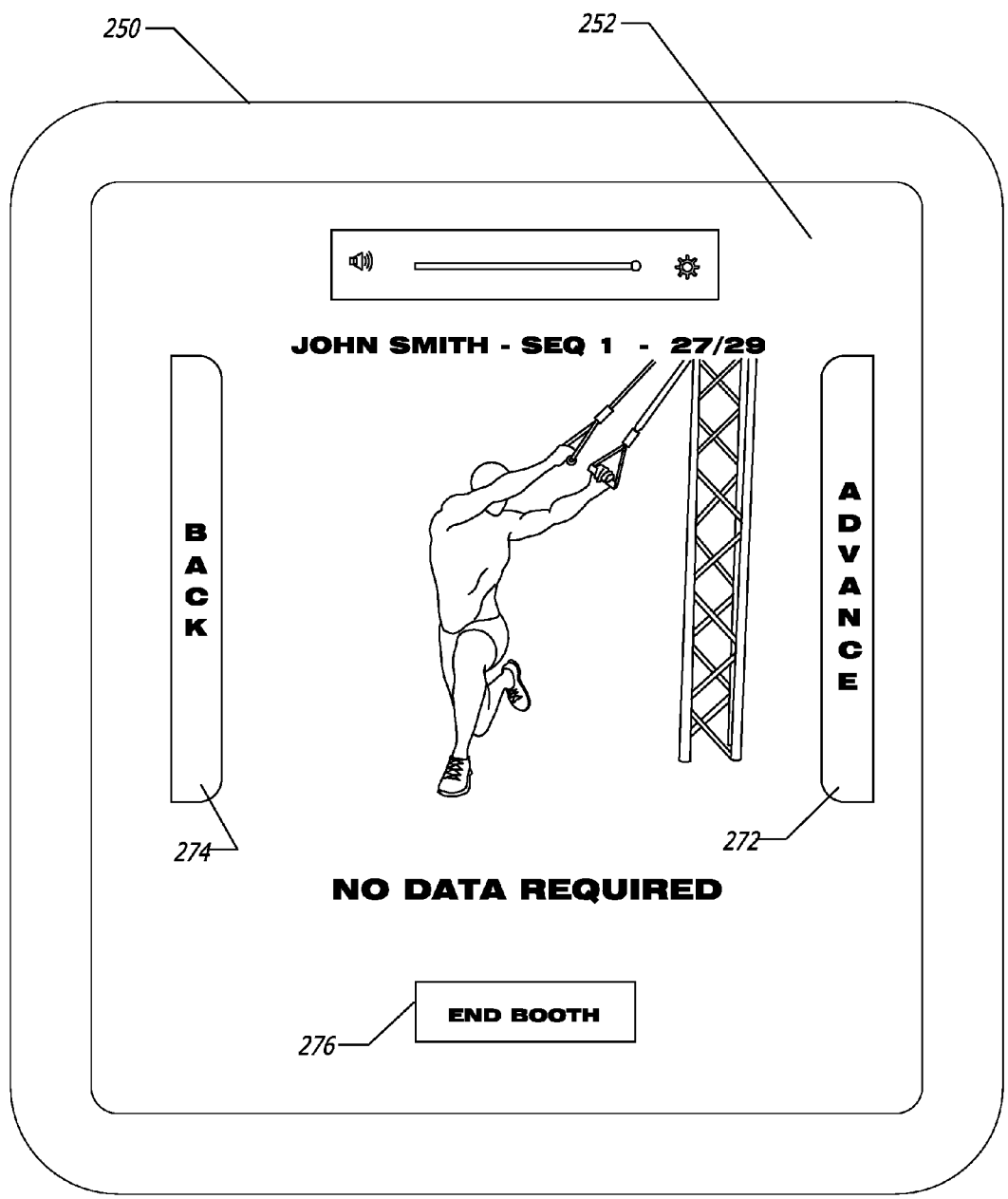

With reference now to FIGS. 35 and 36, as indicated above, the user may pass through a given booth multiple times during the course of his or her workout session. For example, if there are six booths and thirty exercises to be performed, the user will pass through each booth five times. Typically, the same exercise equipment will be present within the booth each time the user passes therethrough. While the user may perform the same exercise each time he or she passes through the booth, it is also contemplated that the user will utilize the exercise equipment within the booth and perform different exercises. For example, when using a universal or multi-purpose exercise device, the device may be adjusted so as to perform a different exercise using that machine when passing through the booth. This can even be accomplished with much less sophisticated and complicated pieces of exercise equipment, such as the resistance bands illustrated in FIGS. 35 and 36. FIG. 31 illustrates the resistance band being used in a squatting motion. FIG. 35 illustrates the resistance bands being used as a triceps pull-down. FIG. 36 illustrates the resistance bands being used in a lunge and rotation full body exercise. Thus, the computerized system of the present invention can take into account a given exercise equipment arrangement for a given booth or set of booths and generate a varied exercise regimen for the user. This can be the case when the user passes through the booths multiple times, or even if the user passes through a sequence of booths only once each, but different booths have the same exercise equipment therein.

Typically in at least a plurality of the booths, if not all of the booths, feedback is entered into the system, such as providing the number of repetitions of the exercise performed at a given weight or resistance. The personal performance data feedback can be sent to the system or can be entered into the handheld electronic device and processed using the software application on the handheld device, or more typically transferred to the local or remote server or computer of the computerized system, such as via wireless network technology. This information is used to determine if the workout prescription needs to be changed either during the current workout session, or more typically in future workout sessions. The computerized system receives the data, typically in the form of number of repetitions performed which are entered in by the user for each exercise station, and based upon predetermined parameters, which may be based at least in part on the user's personal data entered into the system, alters the next workout session for that individual. In effect, each workout is building a profile of information to automatically generate the best possible exercise regimen for the next workout session for that particular individual.

Over time, the system will automatically make gradual changes to the weight or resistance that is being prescribed for each individual based on the number of repetitions the individual did in a previous workout. Thus, the "stress" or weight resistance and/or repetitions are refined and changed over time in order to be adjusted and meet the needs of the user. Based on the previous repetitions, reaction test time, and manual feedback, the workout program or plan for each individual user will be altered. Thus, as the individual gains strength and/or improves his or her fitness level, the system of the present invention automatically alters and adapts the workout program for that individual so as to continue to challenge the individual and increase his or her strength, fitness level, weight management, etc.

The system of the present invention may also incorporate periodization schemes, which alters the stress of training over a period of time. It represents the changes in repetitions or weight or resistance from one workout to the next. Performing the same weight or resistance repeatedly over a prolonged period of time provides limited benefits. Periodization provides schemes based upon research that is designed to get the greatest benefits possible for each individual. These periodization schemes can be based upon the individual user's prior feedback and workout plans (general fitness, strength, muscular endurance/toning, weight management, etc.).

Using the information from the assessments (fitness/strength test, prior workout feedback and/or reaction test) enable the creation of the most comprehensive, automated, personalized exercise prescription available to that individual. The system and method of the present invention gives the average person access to an exercise system that is more complex and sophisticated than heretofore known. The system of the present invention takes the exercise science and applies it to each individual to prescribe the best workout program possible for that individual, with the training based on advanced science and collection of specific information, and making adjustments based on that data over time. It is believed that the more advanced the system, the greater the results will be for each individual.

The computer algorithms of the system can be changed periodically as new data and information on exercise science is advanced. Each gym's central server or a server based in the cloud can dictate the changes to the workout regimens, exercises to be performed throughout the sequence of booths, etc. Preferably, a member's data and exercise regimens are also stored on a cloud-based or central server, such that the member could visit other gym locations and obtain their exact data and up-to-date workout regimen at any of the gym facilities incorporating the present invention.

Aside from the benefit of the automatically generated personalized workout regimen, which is periodically updated, such as from workout session to workout session, the present invention also provides the benefit of the user or member being able to exercise in a private manner. This is believed to assist the user in focusing on the task at hand, preventing over-exertion due to peer pressure, and/or the anxiety that may be experienced by exercising in front of others. When a user or member completes a given booth exercise, each user or member within each booth advances nearly simultaneously to the next booth. This continues until the entire sequence of the booths, and thus the exercise regimen, is completed. It is possible, and in fact preferable, that as a member leaves a given booth a member who is just performing exercises in the immediately preceding booth will enter into that booth. Thus, it is quite possible that each gym member continues and completes all of the booth workout sessions for the day without any interaction with any other gym member, and possibly not even see any other gym member during the entire workout session for that day. Even if other gym members are encountered, such interaction will be brief.

It is anticipated that the amount of time spent within each booth will be fairly limited, such as less than a minute up to a few minutes, and thus the users or members of the gym will be fairly rapidly moving from one booth to another in order to keep up with the sequenced schedule. Thus, it is possible that an exercise facility having thirty sequenced booths could take no more than thirty to forty-five minutes to perform a total exercise workout session for that day utilizing each of the booths for approximately one minute each.

Although the personal performance information may be saved to the handheld electronic device, it may also be relayed in real time to the gym's computer system for immediate collection and processing. Alternatively, upon exiting the last booth, the user swipes the last page or otherwise selects to send the exercise performance results for that workout regimen to the server, such as a cloud-based server via a wireless network, where it immediately processes the information, calculating and preparing the user's next prescribed workout regimen according to a predetermined, but alterable algorithm.

With each of the members or users carrying a handheld electronic device with the downloaded computer application software, emergency issues, such as electrical lighting issues, a medical emergency, etc., may be handled quite easily. An operator of the gym facility may announce over the speaker system that there is an emergency issue and provide instructions to the users. For example, the operator may state "There is an issue in sequence number one, all members please patiently stay in the booth you are now in and we will announce your advancement soon". As soon as the issue is resolved, the operator may announce on the next announcement or queue "Please advance to the next booth", and each user may simply swipe or select the button to move to the next downloaded page representing the next exercise to be performed in the next booth.

It is contemplated by the invention that the downloaded software application to the user's hand-held device will be accessible or usable for a limited period of time. For example, the workout regimen incorporated into the downloaded software application may be used for only one to two hours. Thereafter, the computer application is either removed or otherwise disabled. It is also contemplated that the software application only be capable of being downloaded when within a certain distance of a component of the computerized system, such as a local server. When the user leaves the exercise facility, the computer application may either be removed or disabled. This prevents confusion with a user inadvertently downloading a workout regimen for a particular day, downloading another workout program for another day and confusing the two. It also prevents a user from downloading a personalized workout regimen generated by the invention's computerized system and utilizing it in a location or in a manner not authorized by those owning the exercise facility or otherwise administering the invention.

Use of the computer application and hand-held device allow the user at any time in the future to return to the same gym or to any other gym facility supporting the present invention. Once the user enters their membership number and PIN number on the hand-held device, they can choose from any of the sequences available at that particular gym. The gym may have three sequence choices, or more or less. As the information for the individual's workout is pulled from a cloud-based server, the user is able to visit any gym within the world and retrieve their updated personalized workout regimen.

Moreover, the computer application system downloaded to a handheld device could be used outside of the personal booth sequencing system. For example, in addition to the sequencing system, there could be a generic workout. A predetermined number of pages, such as twenty-nine pages, may prescribe twenty-nine exercises to be performed in sequence at any given gym on generic equipment. Although this might be complicated by the fact that the particular exercise equipment might not be readily available to the user within a gym that does not have the private booths and sequencing system illustrated and described above, it would allow the user to perform the personalized and updated exercise regimen to be performed at any gym, while saving the user's results and subsequently updating the user's exercise regimen for the next workout.

At the end of the workout session for a day, either at the gym or at home or at the office, a user or member may be provided access, either through the handheld electronic device, a mobile device, a desktop computer, etc. access to the user's profile, in which the user can view the results of a given booth, an overview for a workout regimen for that day, monitor progress of the user's exercises and workout sessions, etc. It is contemplated by the present invention that the user could track performance for a given booth or exercise session over time as a way of viewing progress.

It is contemplated by the present invention that although the booths are used in accordance with the workout sequencing program indicated above, the booths instead could be used for other exercise programs. For example, a set of booths could be directed to upper body muscle groups, while another set of booths could be directed to lower body exercises, while yet another set of booths could be directed to core muscle groups, as an example. While this arrangement may not provide an optimal full body exercise regimen, it may be more desirable to some users. The concept of utilizing private booths could also be extended to other types of exercises, such as cardiovascular exercise machines, wherein each booth contains a separate treadmill, stationary bike, elliptical machine, etc. such that the user is able to perform that exercise for the prescribed or desired amount of time in a private setting, while still attending a public gym, and thus obtaining the benefits of a public workout session.

It will be appreciated that the present invention provides many advantages over current methodologies and systems. The automatically generated personalized workout provides the user with a directed workout, and allows the user to relax and have direction. There is no question as to which exercise to do next. The system simply tells the user what exercise to do, at a given weight/resistance, and there is no thought required as to which exercise to perform next. This results in less stress, and no waiting time for equipment. The customer may have the sense that the facility was built specifically for their own personal experience. The privacy aspect of the booths also reduces stress and distractions and allows for better concentration and a more effective workout. The booths are adaptable to the contour and layout of the building, and can be interchangeable. The booths can also present a protected environment with reduced exposure to airborne communicable diseases. Use of the booth system allows the facility to accommodate all of its users, whereas traditional gyms can only handle approximately sixty percent (60%) of their members at any given time. This is due to the fact that the users of the present invention may select and book a particular time for their workout, and will know that each of the booths and exercises will be available to them at that time. However, if a large number of members of a traditional gym were to visit the gym at a particular time, those users may need to wait to access equipment and work stations. The present invention is automated, without the need of data entry or computer programs to assess and enter data. No computer data operators, or even trainers are necessary. This slashes the number of people required to run a gym dramatically. Furthermore, in a gym with as few as three sequences, three members can start every minute, or one hundred eighty members per hour. These members may not see any other members or have any interaction with them during their entire workout regimen, yet receive a highly optimized workout due to the exercise science and computerized system incorporated into the invention. Essentially, the gym member is receiving the services of his or her own personal trainer or exercise physiologist without the need of hiring one of these individuals or scheduling a time with one of these individuals or working out with one of these individuals. These inherent services within the system of the present invention could enable the gym to charge higher fees than traditional gyms.

Although several embodiments have been described in detail for purposes of illustration, various modifications may be made without departing from the scope and spirit of the invention. Accordingly, the invention is not to be limited, except as by the appended claims.

What is claimed is:

1. A process for generating and performing an exercise regimen, comprising the steps of:
   providing a plurality of booths arranged in a predetermined sequence, each booth adapted for use by a single user at a time and each booth being configured to provide privacy to the user in the booth and each booth having an entry and an exit;
   disposing exercise equipment within the booths and/or assigning an exercise to be performed in each booth;
   automatically generating an exercise regimen for each of a plurality of users, including entering user-related data into a computerized system, the exercise regimen comprised of a plurality of exercises to be performed in sequence according to the predetermined sequence of booths; and
   directing the users to perform exercises in the booths corresponding to the users' exercise regimens and the predetermined sequence of booths, wherein the users within the booths move substantially simultaneously from one booth to the next booth in the predetermined sequence of booths.

2. The process of claim 1, including the step of inputting user exercise performance results for each exercise of the exercise regimen into the computerized system.

3. The process of claim 2, including the step of automatically adjusting the user's exercise regimen, using the computerized system, based on the input user exercise performance results.

4. The process of claim 1, wherein the entering user-related data step includes the step of entering physical attributes of the user into the computerized system.

5. The process of claim 4, wherein the physical attributes include age, gender, height, and weight.

6. The process of claim 1, wherein the entering user-related data step includes the step of entering results of an initial fitness determination test performed by the user prior to exercising and generating the exercise regimen, at least in part, based on the results of the initial fitness determination test.

7. The process of claim 6, wherein the initial fitness determination test comprises a grip strength test performed by the user.

8. The process of claim 1, wherein the entering user-related data step includes the step of inputting user desired fitness program into the computerized system.

9. The process of claim 8, wherein the user desired fitness program includes a selection from a general fitness program, weight management program, strength enhancing program, muscle toning program, and a muscle endurance program.

10. The process of claim 1, including the step of the user performing a reaction test immediately prior to performing the sequence of exercises, and automatically adjusting the user's exercise regimen, using the computerized system, based on the reaction test results.

11. The process of claim 1, including the step of providing a hand held electronic device capable of downloading the user's exercise regimen thereto.

12. The process of claim 11, including the step of displaying on an electronic display screen of the hand held electronic device information relating to the exercise to be performed within the booth by the user, according to the user's exercise regimen.

13. The process of claim 11, including the step of entering user exercise performance results into the hand held electronic device.

14. The process of claim 13, including the step of transferring the user performance results from the hand held electronic device to a server computer of the computerized system.

15. The process of claim 1, wherein each booth is assigned a single exercise to be performed by the user.

16. The process of claim 1, wherein each booth has disposed therein a single piece of exercise equipment.

17. The process of claim 1, including the step of displaying on an electronic display screen within the booth information relating to the exercise to be performed within the booth by the user.

18. The process of claim 17, including the step of displaying on the electronic screen user identification, a tutorial of the exercise to be performed in the booth, and a resistance or weight to be used during the exercise by the user.

19. The process of claim 18, wherein the displaying a tutorial of the exercise step includes the step of displaying a photo, animation, video or graphic images on the electronic screen instructing the user how to perform the exercise within each booth.

20. The process of claim 1, wherein the users are directed from booth to booth according to a predetermined time limit for each booth.

21. The process of claim 1, wherein the plurality of booths are interconnected with one another so that users can pass from one booth to an adjoining booth.

22. A process for generating and performing an exercise regimen, comprising the steps of:
automatically generating an exercise regimen for each of a plurality of users, including entering user-related data into a computerized system;
providing a plurality of booths arranged in a predetermined sequence, each booth adapted for use by a single user at a time and each booth being configured to provide privacy to the user in the booth, the booths being interconnected to allow users to move from one booth to an adjacent booth;
assigning each booth a single exercise to be performed in the user's exercise regimen; and
directing the users from one booth to another, substantially simultaneously, according to the predetermined sequence of the booths until the users completes their exercise regimens and/or pass through the sequence of booths.

23. The process of claim 22, wherein each booth has disposed therein a single piece of exercise equipment.

24. The process of claim 22, including the step of displaying on an electronic display screen within the booth information relating to the exercise to be performed within the booth by the user.

25. The process of claim 24, including the step of displaying on the electronic screen user identification, a tutorial of the exercise to be performed in the booth, and a resistance or weight to be used during the exercise by the user.

26. The process of claim 25, wherein the displaying a tutorial of the exercise step includes the step of displaying a photo, animation, video or graphic images on the electronic screen instructing the user how to perform the exercise within each booth.

27. The process of claim 26 wherein the electronic screen comprises an electronic hand held device carried by the user from booth to booth.

28. The process of claim 22, wherein the users are directed from booth to booth according to a predetermined time limit for each booth.

29. A process for generating and performing an exercise regimen, comprising the steps of:
providing a plurality of booths arranged in a predetermined sequence, each booth adapted for use by a single user at a time and each booth being configured to provide privacy to the user in the booth and each booth having an entry and an exit;
directing a plurality of users to each perform an exercise regimen within the booths according to the sequence of booths and exercise equipment disposed within the booth and/or an exercise assigned to each booth; and
periodically notifying the users within the plurality of booths to move to the next booth in the predetermined sequence of booths, so that the users move substantially simultaneously from one booth to the next within the predetermined sequence, until the users complete their exercise regimens and/or pass through the sequence of booths.

30. The process of claim 29, wherein the booths are interconnected with one another so that users can pass from one booth to an adjoining booth.

31. The process of claim 29, including the step of providing a hand held electronic device to a user for displaying the user's exercise regimen, the hand held device being carried from booth to booth during the exercise regimen.

32. The process of claim 31, including the step of entering exercise performance results into a computerized system using the hand held device.

33. The process of claim 29, including the step of displaying on an electronic screen within each booth information related to the exercise to be performed within the booth by the user.

34. The process of claim 33, including the step of displaying on the electronic screen a photo, animation, video or graphic images comprising a tutorial instructing the user how to perform the exercise within each booth.

35. The process of claim 29, including the step of disposing a single piece of exercise equipment within each booth.

36. The process of claim 29, wherein the users are directed to move from one booth to the next booth in the sequence of booths according to a predetermined time period for performing the exercise within the booth.

37. The process of claim 29, including the step of creating the user exercise regimens by entering user-related data into a computerized system.

38. The process of claim 37, wherein the user-related data comprises at least one of physical attributes of the user, results of an initial fitness test performed by the user, and a selection of a user desired fitness program.

* * * * *